US008426204B2

(12) United States Patent
Hammer et al.

(10) Patent No.: US 8,426,204 B2
(45) Date of Patent: Apr. 23, 2013

(54) CHLAMYDOMONAS EPSPS CHLOROPLAST TRANSIT PEPTIDE (CTP) AND EXPRESSION CASSETTES AND TRANSGENIC PLANTS UTILIZING THE CTP

(75) Inventors: Philip E. Hammer, Cary, NC (US); Vadim Beilinson, Cary, NC (US); Todd K. Hinson, Rougemont, NC (US)

(73) Assignee: Athenix Corporation, Morrisville, NC (US)

( * ) Notice: Subject to any disclaimer, the term of this patent is extended or adjusted under 35 U.S.C. 154(b) by 575 days.

(21) Appl. No.: 12/555,175

(22) Filed: Sep. 8, 2009

(65) Prior Publication Data
US 2010/0071090 A1 Mar. 18, 2010

Related U.S. Application Data

(60) Provisional application No. 61/095,134, filed on Sep. 8, 2008.

(51) Int. Cl.
*A01H 5/00* (2006.01)
*C12N 5/04* (2006.01)
*C12N 15/82* (2006.01)

(52) U.S. Cl.
USPC ........... 435/419; 435/418; 800/295; 800/298; 800/300

(58) Field of Classification Search .................. None
See application file for complete search history.

(56) References Cited

U.S. PATENT DOCUMENTS

| 6,570,005 | B1 | 5/2003 | Schnepf et al. | |
|---|---|---|---|---|
| 6,906,245 | B1 * | 6/2005 | Nakajima et al. | 800/300 |
| 2007/0250946 | A1 | 10/2007 | Ascenzi et al. | |
| 2009/0144852 | A1 * | 6/2009 | Tomso et al. | 800/278 |

FOREIGN PATENT DOCUMENTS

| WO | 0226995 | 4/2002 |
|---|---|---|
| WO | 2008039450 | 4/2008 |

OTHER PUBLICATIONS

NCBI Accession XP_001702942.1—5-enolpyruvylshikimate-3-phosphate synthase [*Chlamydomonas reinhardtii*] (2007); pp. 1-2.*
Estruch, Juan J., et al., "VIP3A, a novel *Bacillus thuringiensis* vegetative insecticidal protein with a wide spectrum of activities against lepidopteran insects," *Proc. Natl. Acad. Sci. USA*, May 1996, pp. 5389-5395, vol. 93.
Lee, Mi Kyong, et al., "The Mode of Action of the *Bacillus thuringiensis* Vegetative Insecticidal Protein Vip3A Differs from That of CrylAb δ-Endotoxin," *Applied and Environmental Microbiology*, Aug. 2003, pp. 4648-4657, vol. 69, No. 8.
Liu, J., et al., "Identification of *vip3A*-type genes from *Bacillus thuringiensis* strains and characterization of a novel *vip3A*-type gene," *The Society for Applied Microbiology, Letters in applied Microbiology*, 2007, pp. 432-438, vol. 45.
Funke R. P. et al., "Nucleotide sequence of a cDNA encoding *Chlamydomonas reinhardtii* acetolactate synthase", Plant Physiol, 115, 1997, p. 1288, Uniprot: O22547.
Merchant S. S. et al., "The *Chlamydomonas* genome reveals the evolution of key animal and plant functions", Science, 318, 2007, pp. 245-250, Uniprot: A8JH48_CHLRE.
Roesler, K R et al., "Primary Structure of *Chlamydomonas reinhardtii* Ribulose 1 5-Bisphosphate Carboxylase-Oxygenase Activase and Evidence for a Single Polypeptide", Plant Physiology, vol. 94, No. 4, 1990, pp. 1837-1841.
Kindle Karen L., "Amino-terminal and hydrophobic regions of the *Chlamydomonas reinhardtii* plastocyanin transit peptide are required for efficient protein accumulation in vivo", Plant Molecular Biology, vol. 38, No. 3, Oct. 1998, pp. 365-377.
Leon R et al., "Metabolic engineering of ketocarotenoids biosynthesis in the unicelullar microalga *Chlamydomonas reinhardtii*", Journal of Biotechnology, vol. 130, No. 2, Jun. 15, 2007, pp. 143-152.
Singh B et al., "*Arabidopsis* Acetohydroxyacid Synthase Expressed in *Escherichia coli* is Insensitive to the Feedback Inhibitors", Plant Physiology, vol. 99, No. 2, 1992, pp. 812-816.
Barry, B.D., "The Paradox of Plastic Transit Peptides: Conservation of Function Despite Divergence in Primary Structure," *Biochimica et Biophysica Acta*, 2001, pp. 2-21, vol. 1541.
Chua, N-H. and G.W. Schmidt, "Post-translational Transport into Intact Chloroplasts of a Precursor to the Small Subunit of Ribulose-1,5-Bisphosphate Carboxylase," *Proc. Natl. Acad. Sci. USA*, Dec. 1978, pp. 6110-6114, vol. 75, No. 12.
Lang, M., et al., "Protein Transport into "Complex" Diatom Plastids Utilizes Two Different Targeting Signals," *J. Biol. Chem.*, Nov. 20, 1998, pp. 30973-30978, vol. 273, No. 47.
Mishkind, M.L., et al., "Functional Determinants in Transit Sequences: Import and Partial Maturation by Vascular Plant Chloroplasts of the Ribulose-1,5-Bisphosphate Carboxylase Small Subunit of *Chlamydomonas*," *J. Cell Biol.*, Jan. 1985, pp. 226-234, vol. 100.
Patron, N.J. and R.F. Waller, "Transit Peptide Diversity and Divergence: a Global Analysis of Plastid Targeting Signals," *BioEssays*, 2007, pp. 1048-1058, vol. 29, No. 10.

* cited by examiner

*Primary Examiner* — Cathy Kingdon Worley

(57) ABSTRACT

The present invention provides compositions and methods for targeting polypeptides to the chloroplasts of higher plants. Compositions include expression cassettes having a nucleotide sequence encoding a chloroplast targeting peptide (CTP) operably linked to a nucleotide sequence of interest, wherein the CTP is derived from *Chlamydomonas* sp. Plant transformation vectors, plants and plant cells having the CTP sequences are also encompassed, as well as variants and fragments of the CTP sequences. Methods for expressing a heterologous nucleotide sequence in a plant using the CTP sequences disclosed herein are also provided.

4 Claims, 3 Drawing Sheets

SEQUENCE LISTING

<160> NUMBER OF SEQ ID NOS: 18

<210> SEQ ID NO 1
<211> LENGTH: 297
<212> TYPE: DNA
<213> ORGANISM: Chlamydomonas reinhardtii

<400> SEQUENCE: 1

| | | | | | |
|---|---|---|---|---|---|
| atgaaggccc | tgcgaagtgg | aaccgctgtg | gcgcggggcc | aagcgggctg | tgtttctccc | 60 |
| gctccgcgcc | ctgtgcctat | gtcgtctcag | gcgatgattc | cgagcaccag | ctccccagca | 120 |
| gctcgtgcac | ccgcccggtc | cggtcgccgc | gccctcgctg | tgtcggccaa | gctggctgat | 180 |
| gggtctcgtc | gcatgcagtc | cgaggaggtg | cgccgcgcca | aggaggtggc | ccaggctgcg | 240 |
| ctggccaagg | acagccctgc | cgactgggtg | gaccgctacg | gctcggagcc | gcgcaag | 297 |

<210> SEQ ID NO 2
<211> LENGTH: 297
<212> TYPE: DNA
<213> ORGANISM: Chlamydomonas reinhardtii

<400> SEQUENCE: 2

| | | | | | |
|---|---|---|---|---|---|
| atgaaggccc | tgcgaagtgg | aaccgctgtg | gcgcggggcc | aagcgggctg | tgtttctccc | 60 |
| gctccgcgcc | ctgtgcctat | gtcgtctcag | gcgatgattc | cgagcaccag | ctccccagca | 120 |
| gctcgtgcac | ccgcccggtc | cggtcgccgc | gccctcgctg | tgtcggccaa | gctggctgat | 180 |
| gggtcacgtc | gcatgcagtc | cgaggaggtg | cgccgcgcca | aggaggtggc | ccaggctgcg | 240 |
| ctggctaagg | acagccctgc | cgactgggta | gaccgctacg | gctcggagcc | gcgcaag | 297 |

<210> SEQ ID NO 3
<211> LENGTH: 99
<212> TYPE: PRT
<213> ORGANISM: Chlamydomonas reinhardtii

<400> SEQUENCE: 3

Met Lys Ala Leu Arg Ser Gly Thr Ala Val Ala Arg Gly Gln Ala Gly
 1               5                  10                  15

Cys Val Ser Pro Ala Pro Arg Pro Val Pro Met Ser Ser Gln Ala Met
            20                  25                  30

Ile Pro Ser Thr Ser Ser Pro Ala Ala Arg Ala Pro Ala Arg Ser Gly
        35                  40                  45

Arg Arg Ala Leu Ala Val Ser Ala Lys Leu Ala Asp Gly Ser Arg Arg
    50                  55                  60

Met Gln Ser Glu Glu Val Arg Arg Ala Lys Glu Val Ala Gln Ala Ala
65                  70                  75                  80

Leu Ala Lys Asp Ser Pro Ala Asp Trp Val Asp Arg Tyr Gly Ser Glu
                85                  90                  95

Pro Arg Lys

<210> SEQ ID NO 4
<211> LENGTH: 135
<212> TYPE: DNA
<213> ORGANISM: Chlamydomonas reinhardtii

<400> SEQUENCE: 4

| | | | | | |
|---|---|---|---|---|---|
| atggccgccg | tcattgccaa | gtcctccgtc | tccgcggccg | tggccgcgcc | ggcccgctcc | 60 |
| agcgtgcgcc | ccatggccgc | gctgaagccc | gccgtcaagg | ccgcccccgt | ggctgccccg | 120 | gctcaggcta accag        135

<210> SEQ ID NO 5
<211> LENGTH: 45
<212> TYPE: PRT
<213> ORGANISM: Chlamydomonas reinhardtii

<400> SEQUENCE: 5

```
Met Ala Val Ile Ala Lys Ser Ser Val Ala Ala Val Ala Arg
 1               5                  10                  15

Pro Ala Arg Ser Ser Val Arg Pro Met Ala Ala Leu Lys Pro Ala Val
                20                  25                  30

Lys Ala Ala Pro Val Ala Ala Pro Ala Gln Ala Asn Gln
                35                  40              45
```

<210> SEQ ID NO 6
<211> LENGTH: 225
<212> TYPE: DNA
<213> ORGANISM: Chlamydomonas reinhardtii

<400> SEQUENCE: 6

```
atgcagctgc tcaaccagcg gcaggcgctg cggctgggaa gaagctccgc cagcaagaac      60
cagcaggtgg cgccgctggc atcaaggccg gcaagcagcc tctccgtctc cgcctcctcc     120
gtggcgccgg cgccggcctg ctcggcgccg gcggcgccg ccgccgcgc cgtggtggtg       180 cgcgcctccg ccaccaagga gaaggtggag gagctcacca tccag                    225
```

<210> SEQ ID NO 7
<211> LENGTH: 75
<212> TYPE: PRT
<213> ORGANISM: Chlamydomonas reinhardtii

<400> SEQUENCE: 7

```
Met Gln Leu Leu Asn Gln Arg Gln Ala Leu Arg Leu Gly Arg Ser Ser
 1               5                  10                  15

Ala Ser Lys Asn Gln Gln Val Ala Pro Leu Ala Ser Arg Pro Ala Ser
                20                  25                  30

Ser Leu Ser Val Ser Ala Ser Ser Val Ala Pro Ala Pro Ala Cys Ser
                35                  40                  45

Ala Pro Ala Gly Ala Gly Arg Arg Ala Val Val Arg Ala Ser Ala
                50                  55                  60

Thr Lys Glu Lys Val Glu Glu Leu Thr Ile Gln
 65                  70                  75
```

<210> SEQ ID NO 8
<211> LENGTH: 683
<212> TYPE: PRT
<213> ORGANISM: Chlamydomonas reinhardtii

<400> SEQUENCE: 8

```
Met Lys Ala Leu Arg Ser Gly Thr Ala Val Ala Arg Gly Gln Ala Gly
 1               5                  10                  15

Cys Val Ser Pro Ala Pro Arg Pro Val Pro Met Ser Gln Ala Met
                20                  25                  30

Ile Pro Ser Thr Ser Ser Pro Ala Ala Arg Ala Pro Ala Arg Ser Gly
                35                  40                  45

Arg Arg Ala Leu Ala Val Ser Ala Lys Leu Ala Asp Gly Ser Arg Arg
                50                  55                  60

Met Gln Ser Glu Glu Val Arg Arg Ala Lys Glu Val Ala Gln Ala Ala
 65                  70                  75                  80
```

-continued

Leu Ala Lys Asp Ser Pro Ala Asp Trp Val Asp Arg Tyr Gly Ser Glu
            85                  90                  95

Pro Arg Lys Gly Ala Asp Ile Leu Val Gln Ala Leu Glu Arg Glu Gly
            100                 105                 110

Val Asp Ser Val Phe Ala Tyr Pro Gly Gly Ala Ser Met Glu Ile His
            115                 120                 125

Gln Ala Leu Thr Arg Ser Asp Arg Ile Thr Asn Val Leu Cys Arg His
            130                 135                 140

Glu Gln Gly Glu Ile Phe Ala Ala Glu Gly Tyr Ala Lys Ala Ala Gly
145                 150                 155                 160

Arg Val Gly Val Cys Ile Ala Thr Ser Gly Pro Gly Ala Thr Asn Leu
                165                 170                 175

Val Thr Gly Leu Ala Asp Ala Met Met Asp Ser Ile Pro Leu Val Ala
            180                 185                 190

Ile Thr Gly Gln Val Pro Arg Arg Met Ile Gly Thr Asp Ala Phe Gln
            195                 200                 205

Glu Thr Pro Ile Val Glu Val Thr Arg Ala Ile Thr Lys His Asn Tyr
210                 215                 220

Leu Val Leu Asp Ile Lys Asp Leu Pro Arg Val Ile Lys Glu Ala Phe
225                 230                 235                 240

Tyr Leu Ala Arg Thr Gly Arg Pro Gly Pro Val Leu Val Asp Val Pro
            245                 250                 255

Lys Asp Ile Gln Gln Gln Leu Ala Val Pro Asp Trp Glu Ala Pro Met
            260                 265                 270

Ser Ile Thr Gly Tyr Ile Ser Arg Leu Pro Pro Val Glu Glu Ser
            275                 280                 285

Gln Val Leu Pro Val Leu Arg Ala Leu Gln Gly Ala Ala Lys Pro Val
            290                 295                 300

Ile Tyr Tyr Gly Gly Gly Cys Leu Asp Ala Gln Ala Glu Leu Arg Glu
305                 310                 315                 320

Phe Ala Ala Arg Thr Gly Ile Pro Leu Ala Ser Thr Phe Met Gly Leu
                325                 330                 335

Gly Val Val Pro Ser Thr Asp Pro Asn His Leu Gln Met Leu Gly Met
            340                 345                 350

His Gly Thr Val Phe Ala Asn Tyr Ala Val Asp Gln Ala Asp Leu Leu
            355                 360                 365

Val Ala Leu Gly Val Arg Phe Asp Asp Arg Val Thr Gly Lys Leu Asp
370                 375                 380

Ala Phe Ala Ala Arg Ala Arg Ile Val His Ile Asp Ile Asp Ala Ala
385                 390                 395                 400

Glu Ile Ser Lys Asn Lys Thr Ala His Val Pro Val Cys Gly Asp Val
            405                 410                 415

Lys Gln Ala Leu Ser His Leu Asn Arg Leu Leu Ala Ala Glu Pro Leu
            420                 425                 430

Pro Ala Asp Lys Trp Ala Gly Trp Arg Ala Glu Leu Ala Ala Lys Arg
            435                 440                 445

Ala Glu Phe Pro Met Arg Tyr Pro Gln Arg Asp Asp Ala Ile Val Pro
            450                 455                 460

Gln His Ala Ile Gln Val Leu Gly Glu Glu Thr Gln Gly Glu Ala Ile
465                 470                 475                 480

Ile Thr Thr Gly Val Gly Gln His Gln Met Trp Ala Ala Gln Trp Tyr
            485                 490                 495

Pro Tyr Lys Glu Thr Arg Arg Trp Ile Ser Ser Gly Gly Leu Gly Ser

```
            500                 505                 510
Met Gly Phe Gly Leu Pro Ala Ala Leu Gly Ala Val Ala Phe Asp
            515                 520                 525

Gly Lys Asn Gly Arg Pro Lys Lys Thr Val Val Asp Ile Asp Gly Asp
        530                 535                 540

Gly Ser Phe Leu Met Asn Val Gln Glu Leu Ala Thr Ile Phe Ile Glu
545                 550                 555                 560

Lys Leu Asp Val Lys Val Met Leu Leu Asn Asn Gln His Leu Gly Met
                565                 570                 575

Val Val Gln Trp Glu Asp Arg Phe Tyr Lys Ala Asn Arg Ala His Thr
            580                 585                 590

Tyr Leu Gly Lys Arg Glu Ser Glu Trp His Ala Thr Gln Asp Glu Glu
            595                 600                 605

Asp Ile Tyr Pro Asn Phe Val Asn Met Ala Gln Ala Phe Gly Val Pro
        610                 615                 620

Ser Arg Arg Val Ile Val Lys Glu Gln Leu Arg Gly Ala Ile Arg Thr
625                 630                 635                 640

Met Leu Asp Thr Pro Gly Pro Tyr Leu Leu Glu Val Met Val Pro His
                645                 650                 655

Ile Glu His Val Leu Pro Met Ile Pro Gly Gly Ala Ser Phe Lys Asp
                660                 665                 670

Ile Ile Thr Glu Gly Asp Gly Thr Val Lys Tyr
            675                 680

<210> SEQ ID NO 9
<211> LENGTH: 185
<212> TYPE: PRT
<213> ORGANISM: Chlamydomonas reinhardtii

<400> SEQUENCE: 9

Met Ala Ala Val Ile Ala Lys Ser Ser Val Ser Ala Ala Val Ala Arg
  1               5                  10                  15

Pro Ala Arg Ser Ser Val Arg Pro Met Ala Ala Leu Lys Pro Ala Val
                20                  25                  30

Lys Ala Ala Pro Val Ala Ala Pro Ala Gln Ala Asn Gln Met Met Val
            35                  40                  45

Trp Thr Pro Val Asn Asn Lys Met Phe Glu Thr Phe Ser Tyr Leu Pro
        50                  55                  60

Pro Leu Ser Asp Glu Gln Ile Ala Ala Gln Val Asp Tyr Ile Val Ala
65                  70                  75                  80

Asn Gly Trp Ile Pro Cys Leu Glu Phe Ala Glu Ser Asp Lys Ala Tyr
                85                  90                  95

Val Ser Asn Glu Ser Ala Ile Arg Phe Gly Ser Val Ser Cys Leu Tyr
                100                 105                 110

Tyr Asp Asn Arg Tyr Trp Thr Met Trp Lys Leu Pro Met Phe Gly Cys
            115                 120                 125

Arg Asp Pro Met Gln Val Leu Arg Glu Ile Val Ala Cys Thr Lys Ala
        130                 135                 140

Phe Pro Asp Ala Tyr Val Arg Leu Val Ala Phe Asp Asn Gln Lys Gln
145                 150                 155                 160

Val Gln Ile Met Gly Phe Leu Val Gln Arg Pro Lys Ser Ala Arg Asp
                165                 170                 175

Trp Gln Pro Ala Asn Lys Arg Ser Val
            180                 185
```

```
<210> SEQ ID NO 10
<211> LENGTH: 512
<212> TYPE: PRT
<213> ORGANISM: Chlamydomonas reinhardtii

<400> SEQUENCE: 10

Met Gln Leu Leu Asn Gln Arg Gln Ala Leu Arg Leu Gly Arg Ser Ser
 1               5                  10                  15

Ala Ser Lys Asn Gln Gln Val Ala Pro Leu Ala Ser Arg Pro Ala Ser
            20                  25                  30

Ser Leu Ser Val Ser Ala Ser Val Ala Pro Ala Pro Ala Cys Ser
        35                  40                  45

Ala Pro Ala Gly Ala Gly Arg Arg Ala Val Val Arg Ala Ser Ala
    50                  55                  60

Thr Lys Glu Lys Val Glu Glu Leu Thr Ile Gln Pro Val Lys Lys Ile
 65                  70                  75                  80

Ala Gly Thr Val Lys Leu Pro Gly Ser Lys Ser Leu Ser Asn Arg Ile
                85                  90                  95

Leu Leu Leu Ala Ala Leu Ser Glu Gly Thr Thr Leu Val Lys Asn Leu
            100                 105                 110

Leu Asp Ser Asp Asp Ile Arg Tyr Met Val Gly Ala Leu Lys Ala Leu
        115                 120                 125

Asn Val Lys Leu Glu Glu Asn Trp Glu Ala Gly Glu Met Val Val His
    130                 135                 140

Gly Cys Gly Gly Arg Phe Asp Ser Ala Gly Ala Glu Leu Phe Leu Gly
145                 150                 155                 160

Asn Ala Gly Thr Ala Met Arg Pro Leu Thr Ala Ala Val Val Ala Ala
                165                 170                 175

Gly Arg Gly Lys Phe Val Leu Asp Gly Val Ala Arg Met Arg Glu Arg
            180                 185                 190

Pro Ile Glu Asp Leu Val Asp Gly Leu Val Gln Leu Gly Val Asp Ala
        195                 200                 205

Lys Cys Thr Met Gly Thr Gly Cys Pro Pro Val Glu Val Asn Ser Lys
    210                 215                 220

Gly Leu Pro Thr Gly Lys Val Tyr Leu Ser Gly Lys Val Ser Ser Gln
225                 230                 235                 240

Tyr Leu Thr Ala Leu Leu Met Ala Ala Pro Leu Ala Val Pro Gly Gly
                245                 250                 255

Ala Gly Gly Asp Ala Ile Glu Ile Ile Lys Asp Glu Leu Val Ser
            260                 265                 270

Gln Pro Tyr Val Asp Met Thr Val Lys Leu Met Glu Arg Phe Gly Val
        275                 280                 285

Val Val Glu Arg Leu Asn Gly Leu Gln His Leu Arg Ile Pro Ala Gly
    290                 295                 300

Gln Thr Tyr Lys Thr Pro Gly Glu Ala Tyr Val Glu Gly Asp Ala Ser
305                 310                 315                 320

Ser Ala Ser Tyr Phe Leu Ala Gly Ala Thr Ile Thr Gly Gly Thr Val
                325                 330                 335

Thr Val Glu Gly Cys Gly Ser Asp Ser Leu Gln Gly Asp Val Arg Phe
            340                 345                 350

Ala Glu Val Met Gly Leu Leu Gly Ala Lys Val Glu Trp Ser Pro Tyr
        355                 360                 365

Ser Ile Thr Ile Thr Gly Pro Ser Ala Phe Gly Lys Pro Ile Thr Gly
    370                 375                 380

Ile Asp His Asp Cys Asn Asp Ile Pro Asp Ala Ala Met Thr Leu Ala
```

|     |     |     | 385 |     |     |     |     | 390 |     |     |     |     | 395 |     |     |     |     | 400 |
|-----|-----|-----|-----|-----|-----|-----|-----|-----|-----|-----|-----|-----|-----|-----|-----|-----|-----|-----|

Val Ala Ala Leu Phe Ala Asp Arg Pro Thr Ala Ile Arg Asn Val Tyr
                405                 410                 415

Asn Trp Arg Val Lys Glu Thr Glu Arg Met Val Ala Ile Val Thr Glu
                420                 425                 430

Leu Arg Lys Leu Gly Ala Glu Val Glu Glu Gly Arg Asp Tyr Cys Ile
                435                 440                 445

Val Thr Pro Pro Gly Gly Val Lys Gly Val Lys Ala Asn Val Gly
                450                 455                 460

Ile Asp Thr Tyr Asp Asp His Arg Met Ala Met Ala Phe Ser Leu Val
465                 470                 475                 480

Ala Ala Ala Gly Val Pro Val Val Ile Arg Asp Pro Gly Cys Thr Arg
                485                 490                 495

Lys Thr Phe Pro Thr Tyr Phe Lys Val Phe Glu Ser Val Ala Gln His
                500                 505                 510

<210> SEQ ID NO 11
<211> LENGTH: 1602
<212> TYPE: DNA
<213> ORGANISM: Artificial Sequence
<220> FEATURE:
<223> OTHER INFORMATION: synthetic ChlamyAHAS/GRG1 construct

<400> SEQUENCE: 11

```
atgaaggccc tgcgaagtgg aaccgctgtg gcgcggggcc aagcgggctg tgtttctccc      60
gctccgcgcc ctgtgcctat gtcgtctcag gcgatgattc cgagcaccag ctccccagca     120
gctcgtgcac ccgcccggtc cggtcgccgc gccctcgctg tgtcggccaa gctggctgat     180
gggtctcgtc gcatgcagtc cgaggaggtg cgccgcgcca aggaggtggc ccaggctgcg     240
ctggccaagg acagccctgc cgactgggtg daccgctacg gctcggagcc gcgcaaggga     300
tccggcatga aggtgacaat ccagcctggc gatctcacag gcatcattca gagcccagcg     360
tcaaagtctt caatgcagag agcgtgcgcg gcggccctgg tggcgaaggg gatctcagaa     420
atcatcaacc tgggcatag caacgatgat aaggccgcga gagatatcgt gagccgtctt     480
ggggccagac ttgaagatca gccagatggc agcctccaga tcacttcaga aggcgttaag     540
ccagtggcgc cttcatcga ttgcggggaa tcagggctgt ctatccgcat gttcacacca     600
atcgtggcgc tctcaaagga agaagtgaca atcaaggggt cagggtcact cgttactcgc     660
cctatggatt tcttcgatga aatcctgcca catctgggcg tgaaggtgaa gtcaaatcag     720
gggaagctcc ctctggttat ccaggggcca cttaagccag cggatgttac agttgatggg     780
tctctctcat ctcagttcct gacaggcctc ctgcttgcct acgccgcggc ggatgccagc     840
gatgttgcca tcaaggtgac taacctgaag tcacgtcctt acatcgatct tactcttgat     900
gttatgaagc gttcggcct caagactcct gaaaaccgca actacgaaga gttctacttc     960
aaggccggga acgtgtacga cgaaacaaag atgcagcgtt acactgttga aggggattgg    1020
tcagggggcg cgttcctgct cgttgcgggg gccatcgccg gccaatcac tgttcgtggc    1080
cttgatatcg cgtcaactca ggcggataag gcgatcgttc aggcgctcat gagcgccaac    1140
gccgggatcg cgatcgatgc caaggaaatc aagctgcatc ctgccgatct gaacgccttc    1200
gagttcgatg ccactgattg ccctgatctc ttcccaccac tcgtggccct cgcctcatac    1260
tgcaagggg aaacaaagat caagggcgtg agccgccttg cgcataagga atctgataga    1320
gggctgactc ttcaggatga gttcgggaag atgggcgttg aaatccatct gaagggggat    1380
ctcatgcgtg tgatcggcgg gaaggggtg aagggcgccg aagttagctc acgtcatgat    1440
```

-continued catcgcatcg ccatggcgtg cgccgtggcg gcgctcaagg ccgttgggga acaacaatc        1500 gaacatgccg aagcggttaa caagtcttac cctgatttct actcagattt gaagcagctc      1560
gggggcgtgg tgtctctgaa ccatcagttc aacttctctt ag                          1602

<210> SEQ ID NO 12
<211> LENGTH: 533
<212> TYPE: PRT
<213> ORGANISM: Artificial Sequence
<220> FEATURE:
<223> OTHER INFORMATION: synthetic ChlamyAHAS/GRG1 construct

<400> SEQUENCE: 12

Met Lys Ala Leu Arg Ser Gly Thr Ala Val Ala Arg Gly Gln Ala Gly
1               5                   10                  15

Cys Val Ser Pro Ala Pro Arg Pro Val Pro Met Ser Ser Gln Ala Met
            20                  25                  30

Ile Pro Ser Thr Ser Ser Pro Ala Ala Arg Ala Pro Ala Arg Ser Gly
        35                  40                  45

Arg Arg Ala Leu Ala Val Ser Ala Lys Leu Ala Asp Gly Ser Arg Arg
    50                  55                  60

Met Gln Ser Glu Glu Val Arg Arg Ala Lys Glu Val Ala Gln Ala Ala
65                  70                  75                  80

Leu Ala Lys Asp Ser Pro Ala Asp Trp Val Arg Tyr Gly Ser Glu
                85                  90                  95

Pro Arg Lys Gly Ser Gly Met Lys Val Thr Ile Gln Pro Gly Asp Leu
            100                 105                 110

Thr Gly Ile Ile Gln Ser Pro Ala Ser Lys Ser Ser Met Gln Arg Ala
        115                 120                 125

Cys Ala Ala Leu Val Ala Lys Gly Ile Ser Glu Ile Ile Asn Pro
    130                 135                 140

Gly His Ser Asn Asp Lys Ala Ala Arg Asp Ile Val Ser Arg Leu
145                 150                 155                 160

Gly Ala Arg Leu Glu Asp Gln Pro Asp Gly Ser Leu Gln Ile Thr Ser
                165                 170                 175

Glu Gly Val Lys Pro Val Ala Pro Phe Ile Asp Cys Gly Glu Ser Gly
            180                 185                 190

Leu Ser Ile Arg Met Phe Thr Pro Ile Val Ala Leu Ser Lys Glu Glu
        195                 200                 205

Val Thr Ile Lys Gly Ser Gly Ser Leu Val Thr Arg Pro Met Asp Phe
    210                 215                 220

Phe Asp Glu Ile Leu Pro His Leu Gly Val Lys Val Lys Ser Asn Gln
225                 230                 235                 240

Gly Lys Leu Pro Leu Val Ile Gln Gly Pro Leu Lys Pro Ala Asp Val
                245                 250                 255

Thr Val Asp Gly Ser Leu Ser Ser Gln Phe Leu Thr Gly Leu Leu Leu
            260                 265                 270

Ala Tyr Ala Ala Asp Ala Ser Asp Val Ala Ile Lys Val Thr Asn
        275                 280                 285

Leu Lys Ser Arg Pro Tyr Ile Asp Leu Thr Leu Asp Val Met Lys Arg
    290                 295                 300

Phe Gly Leu Lys Thr Pro Glu Asn Arg Asn Tyr Glu Glu Phe Tyr Phe
305                 310                 315                 320

Lys Ala Gly Asn Val Tyr Asp Glu Thr Lys Met Gln Arg Tyr Thr Val
                325                 330                 335

```
Glu Gly Asp Trp Ser Gly Gly Ala Phe Leu Leu Val Ala Gly Ala Ile
            340                 345                 350
Ala Gly Pro Ile Thr Val Arg Gly Leu Asp Ile Ala Ser Thr Gln Ala
        355                 360                 365
Asp Lys Ala Ile Val Gln Ala Leu Met Ser Ala Asn Ala Gly Ile Ala
    370                 375                 380
Ile Asp Ala Lys Glu Ile Lys Leu His Pro Ala Asp Leu Asn Ala Phe
385                 390                 395                 400
Glu Phe Asp Ala Thr Asp Cys Pro Asp Leu Phe Pro Pro Leu Val Ala
            405                 410                 415
Leu Ala Ser Tyr Cys Lys Gly Glu Thr Lys Ile Lys Gly Val Ser Arg
        420                 425                 430
Leu Ala His Lys Glu Ser Asp Arg Gly Leu Thr Leu Gln Asp Glu Phe
    435                 440                 445
Gly Lys Met Gly Val Glu Ile His Leu Glu Gly Asp Leu Met Arg Val
450                 455                 460
Ile Gly Gly Lys Gly Val Lys Gly Ala Glu Val Ser Ser Arg His Asp
465                 470                 475                 480
His Arg Ile Ala Met Ala Cys Ala Val Ala Ala Leu Lys Ala Val Gly
            485                 490                 495
Glu Thr Thr Ile Glu His Ala Glu Ala Val Asn Lys Ser Tyr Pro Asp
        500                 505                 510
Phe Tyr Ser Asp Leu Lys Gln Leu Gly Gly Val Val Ser Leu Asn His
    515                 520                 525
Gln Phe Asn Phe Ser
    530

<210> SEQ ID NO 13
<211> LENGTH: 1413
<212> TYPE: DNA
<213> ORGANISM: Artificial Sequence
<220> FEATURE:
<223> OTHER INFORMATION: synthetic ChlamyAHAS/GRG8 construct

<400> SEQUENCE: 13
ctgcagacca tggccgccgt cattgccaag tcctccgtct ccgcggccgt ggcccgcccg     60
gcccgctcca gcgtgcgccc catggccgcg ctgaagcccg ccgtcaaggc cgcccccgtg    120
gctgccccgg ctcaggctaa ccagggatcc ggcatgatga tgggtagagc caaactcacg    180
attatcccgc cgggcaagcc tttgaccgga cgcgccatgc cgccgggatc gaagtcgatc    240
accaaccgcg cattgctgct cgccggcctc gccaagggca cgagccggct aaccggtgcg    300
ctgaagagcg acgatacccg ctatatggcc gaagcgctgc gtgcgatggg tgtaacgatc    360
gacgagcccg acgacaccac gttcatcgtc aaaggcagcg gcaagctgca gccgccggca    420
gccccgcttt cctcggcaa tgccggcacg gcaacgcgct tcctgacggc ggccgcggca    480
ctggtggacg gcaaggtcat cgtcgacggc gatgcccata tgcgcaagcg gccgatcgga    540
ccgctagtcg acgcgttgcg ctcgctcggc atcgatgcct cggctgaaac cggctgcccg    600
ccagtcacga tcaacggcac cggccgcttc gaggcaagcc gcgtgcagat cgatggcggc    660
ctgtccagcc agtatgtctc ggcgctcctg atgatggccg ccggcggcga tcgcgctgtc    720
gatgtcgagc ttctcggcga acatatcggc gctctcggct atatcgacct gaccgttgcc    780
gccatgcgcg ctttcggcgc gaaggttgag cgtgtgagcc ggtcgcctg gcgcgtcgag    840 cccaccggct atcatgcggc cgacttcgtg atcgagccgg atgcctctgc tgcgacctat    900
ctctgggccg ccgaagttct gagcggcggc aagatcgatc tcggcacgcc ggcggaacag    960
```

```
ttctcgcaac cggatgcgaa agcctatgat ctgatttcga aattcccgca tctgcctgct    1020
gtcatcgacg gctcgcagat gcaggacgcc atcccgacgc tcgccgttct cgccgctttc    1080
aacgaaatgc ctgtgcgctt cgtcggtatc gaaaacctgc gcgtcaagga atgcgatcgt    1140
atccgcgcgc tctcgagcgg cctatcccgc atcgttccga acctcggcac ggaagagggc    1200
gacgatctca tcatcgcctc cgatccgagc cttgccggca aaatcctgac cgcagagatc    1260
gatagctttg ccgatcaccg catcgccatg agctttgcgc tggccggcct gaagatcggc    1320
ggcattacca ttctcgaccc cgactgcgtc gccaagacat cccgtccta ctggaatgtg    1380 ctgtcttcgc tggggtcgc ctacgaagac tga                                  1413
```

<210> SEQ ID NO 14
<211> LENGTH: 467
<212> TYPE: PRT
<213> ORGANISM: Artificial Sequence
<220> FEATURE:
<223> OTHER INFORMATION: synthetic ChlamyAHAS/GRG8 construct

<400> SEQUENCE: 14

```
Met Ala Ala Val Ile Ala Lys Ser Ser Val Ala Ala Val Ala Arg
 1               5                  10                  15

Pro Ala Arg Ser Ser Val Arg Pro Met Ala Ala Leu Lys Pro Ala Val
                20                  25                  30

Lys Ala Ala Pro Val Ala Ala Pro Ala Gln Ala Asn Gln Gly Ser Gly
            35                  40                  45

Met Met Met Gly Arg Ala Lys Leu Thr Ile Ile Pro Pro Gly Lys Pro
        50                  55                  60

Leu Thr Gly Arg Ala Met Pro Pro Gly Ser Lys Ser Ile Thr Asn Arg
65                  70                  75                  80

Ala Leu Leu Leu Ala Gly Leu Ala Lys Gly Thr Ser Arg Leu Thr Gly
                85                  90                  95

Ala Leu Lys Ser Asp Asp Thr Arg Tyr Met Ala Glu Ala Leu Arg Ala
            100                 105                 110

Met Gly Val Thr Ile Asp Glu Pro Asp Thr Thr Phe Ile Val Lys
        115                 120                 125

Gly Ser Gly Lys Leu Gln Pro Pro Ala Ala Pro Leu Phe Leu Gly Asn
130                 135                 140

Ala Gly Thr Ala Thr Arg Phe Leu Thr Ala Ala Ala Leu Val Asp
145                 150                 155                 160

Gly Lys Val Ile Val Asp Gly Asp Ala His Met Arg Lys Arg Pro Ile
                165                 170                 175

Gly Pro Leu Val Asp Ala Leu Arg Ser Leu Gly Ile Asp Ala Ser Ala
            180                 185                 190

Glu Thr Gly Cys Pro Pro Val Thr Ile Asn Gly Thr Gly Arg Phe Glu
        195                 200                 205

Ala Ser Arg Val Gln Ile Asp Gly Gly Leu Ser Ser Gln Tyr Val Ser
    210                 215                 220

Ala Leu Leu Met Met Ala Ala Gly Gly Asp Arg Ala Val Asp Val Glu
225                 230                 235                 240

Leu Leu Gly Glu His Ile Gly Ala Leu Gly Tyr Ile Asp Leu Thr Val
                245                 250                 255

Ala Ala Met Arg Ala Phe Gly Ala Lys Val Glu Arg Val Ser Pro Val
            260                 265                 270

Ala Trp Arg Val Glu Pro Thr Gly Tyr His Ala Ala Asp Phe Val Ile
        275                 280                 285
```

```
Glu Pro Asp Ala Ser Ala Ala Thr Tyr Leu Trp Ala Ala Glu Val Leu
    290                 295                 300

Ser Gly Gly Lys Ile Asp Leu Gly Thr Pro Ala Glu Gln Phe Ser Gln
305                 310                 315                 320

Pro Asp Ala Lys Ala Tyr Asp Leu Ile Ser Lys Phe Pro His Leu Pro
                325                 330                 335

Ala Val Ile Asp Gly Ser Gln Met Gln Asp Ala Ile Pro Thr Leu Ala
            340                 345                 350

Val Leu Ala Ala Phe Asn Glu Met Pro Val Arg Phe Val Gly Ile Glu
        355                 360                 365

Asn Leu Arg Val Lys Glu Cys Asp Arg Ile Arg Ala Leu Ser Ser Gly
    370                 375                 380

Leu Ser Arg Ile Val Pro Asn Leu Gly Thr Glu Glu Gly Asp Asp Leu
385                 390                 395                 400

Ile Ile Ala Ser Asp Pro Ser Leu Ala Gly Lys Ile Leu Thr Ala Glu
                405                 410                 415

Ile Asp Ser Phe Ala Asp His Arg Ile Ala Met Ser Phe Ala Leu Ala
            420                 425                 430

Gly Leu Lys Ile Gly Gly Ile Thr Ile Leu Asp Pro Asp Cys Val Ala
        435                 440                 445

Lys Thr Phe Pro Ser Tyr Trp Asn Val Leu Ser Ser Leu Gly Val Ala
    450                 455                 460

Tyr Glu Asp
465

<210> SEQ ID NO 15
<211> LENGTH: 1548
<212> TYPE: DNA
<213> ORGANISM: Artificial Sequence
<220> FEATURE:
<223> OTHER INFORMATION: synthetic ChlamyEPSPS/GRG23(ace3)(R173K)
      construct

<400> SEQUENCE: 15
atgaaggccc tgcgaagtgg aaccgctgtg gcgcggggcc aagcgggctg tgtttctccc      60
gctccgcgcc ctgtgcctat gtcgtctcag gcgatgattc gagcaccag ctccccagca     120 gctcgtgcac ccgcccggtc cggtcgccgc ccctcgctg tgtcggccaa gctggctgat     180
gggtctcgtc gcatgcagtc cgaggaggtg cgccgcgcca aggaggtggc ccaggctgcg     240
ctggccaagg acagccctgc cgactgggtg gaccgctacg gctcggagcc gcgcaaggga     300
tccggcatgg aaactgatcg ccttgtgatc ccaggatcga aaagcatcac caaccgggct     360
ttgcttttgg ctgccgcagc gaagggcacg tcggtcctgg tgagaccatt ggtcagcgcc     420 gataccctcag cattcaaaac tgcaatccag ccctcggtg ccaacgtctc agccgacggt     480
gacgattggg tcgttgaagg cctgggtcag gcacccaacc tcgacgccga catctggtgc     540
gaggacgcag gtactgtggc ccggttcctc cctccattcg tagccgcagg tcaggggaag     600
ttcaccgtcg acggatcaga gcagctgcgg cggcgcccgc ttcggcccgt ggtcgacggc     660
atccgccacc tgggcgcccg cgtctcctcc gagcagctgc cccttacaat tgaagcgagc     720
gggctggcag gcgggagta cgaaattgaa gcccatcaga gcagccagtt cgcctccggc     780
ctgatcatgg ccgccccgta cgcgagacaa ggcctgcgtg tgcggatacc aaatcccgtg     840
tcacagccct acctcacgat gacactgcgg atgatgaggg acttcggcat tgagaccagc     900
accgacggag ccaccgtcag cgtccctcca gggcgctaca cagcccggcg gtatgaaata     960
```

```
gaaccggatg cgtcaactgc gtcgtacttc gccgccgctt ccgccgtctc tggcaggcgc    1020
ttcgaatttc aaggccttgg cacagacagc atccaaggcg acacgtcatt cttcaatgta    1080
cttgggcggc tcggtgcgga ggtccactgg gcatccaact cggtcaccat acggggaccg    1140
gaaaggctga ccggcgacat tgaagtggat atgggcgaga tttcggacac cttcatgaca    1200
ctcgcggcga ttgcccettt ggccgatgga cccatcacga taaccaacat tggtcatgca    1260
cggttgaagg aatccgaccg catctcagcg atggaaagca acctgcgcac gctcggtgta    1320
caaaccgacg tcggacacga ctggatgaga atctacccct ctaccccgca cggcggtaga    1380
gtgaattgcc accgggacca caggatcgct atggcgtttt caatcctggg actgagagtg    1440
gacgggatta ccctcgacga ccctcaatgc gtcgggaaga cctttcctgg cttcttcgac    1500
taccttggac gccttttccc cgaaaaggcg cttacgctcc ccggctag              1548

<210> SEQ ID NO 16
<211> LENGTH: 515
<212> TYPE: PRT
<213> ORGANISM: Artificial Sequence
<220> FEATURE:
<223> OTHER INFORMATION: synthetic ChlamyEPSPS/GRG23(ace3)(R173K)
      construct

<400> SEQUENCE: 16

Met Lys Ala Leu Arg Ser Gly Thr Ala Val Arg Gly Gln Ala Gly
  1               5                  10                  15

Cys Val Ser Pro Ala Pro Arg Pro Val Pro Met Ser Ser Gln Ala Met
                 20                  25                  30

Ile Pro Ser Thr Ser Ser Pro Ala Ala Arg Ala Pro Ala Arg Ser Gly
             35                  40                  45

Arg Arg Ala Leu Ala Val Ser Ala Lys Leu Ala Asp Gly Ser Arg Arg
         50                  55                  60

Met Gln Ser Glu Glu Val Arg Arg Ala Lys Glu Val Ala Gln Ala Ala
 65                  70                  75                  80

Leu Ala Lys Asp Ser Pro Ala Asp Trp Val Asp Arg Tyr Gly Ser Glu
                 85                  90                  95

Pro Arg Lys Gly Ser Gly Met Glu Thr Asp Arg Leu Val Ile Pro Gly
            100                 105                 110

Ser Lys Ser Ile Thr Asn Arg Ala Leu Leu Leu Ala Ala Ala Lys
            115                 120                 125

Gly Thr Ser Val Leu Val Arg Pro Leu Val Ser Ala Asp Thr Ser Ala
        130                 135                 140

Phe Lys Thr Ala Ile Gln Ala Leu Gly Ala Asn Val Ser Ala Asp Gly
145                 150                 155                 160

Asp Asp Trp Val Val Glu Gly Leu Gly Gln Ala Pro Asn Leu Asp Ala
                165                 170                 175

Asp Ile Trp Cys Glu Asp Ala Gly Thr Val Ala Arg Phe Leu Pro Pro
            180                 185                 190

Phe Val Ala Ala Gly Gln Gly Lys Phe Thr Val Asp Gly Ser Glu Gln
        195                 200                 205

Leu Arg Arg Arg Pro Leu Arg Pro Val Val Asp Gly Ile Arg His Leu
    210                 215                 220

Gly Ala Arg Val Ser Ser Glu Gln Leu Pro Leu Thr Ile Glu Ala Ser
225                 230                 235                 240

Gly Leu Ala Gly Gly Glu Tyr Glu Ile Glu Ala His Gln Ser Ser Gln
                245                 250                 255

Phe Ala Ser Gly Leu Ile Met Ala Ala Pro Tyr Ala Arg Gln Gly Leu
```

```
                    260                 265                 270
Arg Val Arg Ile Pro Asn Pro Val Ser Gln Pro Tyr Leu Thr Met Thr
            275                 280                 285
Leu Arg Met Met Arg Asp Phe Gly Ile Glu Thr Ser Thr Asp Gly Ala
        290                 295                 300
Thr Val Ser Val Pro Pro Gly Arg Tyr Thr Ala Arg Arg Tyr Glu Ile
305                 310                 315                 320
Glu Pro Asp Ala Ser Thr Ala Ser Tyr Phe Ala Ala Ser Ala Val
                325                 330                 335
Ser Gly Arg Arg Phe Glu Phe Gln Gly Leu Gly Thr Asp Ser Ile Gln
            340                 345                 350
Gly Asp Thr Ser Phe Phe Asn Val Leu Gly Arg Leu Gly Ala Glu Val
        355                 360                 365
His Trp Ala Ser Asn Ser Val Thr Ile Arg Gly Pro Glu Arg Leu Thr
    370                 375                 380
Gly Asp Ile Glu Val Asp Met Gly Glu Ile Ser Asp Thr Phe Met Thr
385                 390                 395                 400
Leu Ala Ala Ile Ala Pro Leu Ala Asp Gly Pro Ile Thr Ile Thr Asn
                405                 410                 415
Ile Gly His Ala Arg Leu Lys Glu Ser Asp Arg Ile Ser Ala Met Glu
            420                 425                 430
Ser Asn Leu Arg Thr Leu Gly Val Gln Thr Asp Val Gly His Asp Trp
        435                 440                 445
Met Arg Ile Tyr Pro Ser Thr Pro His Gly Gly Arg Val Asn Cys His
    450                 455                 460
Arg Asp His Arg Ile Ala Met Ala Phe Ser Ile Leu Gly Leu Arg Val
465                 470                 475                 480
Asp Gly Ile Thr Leu Asp Asp Pro Gln Cys Val Gly Lys Thr Phe Pro
                485                 490                 495
Gly Phe Phe Asp Tyr Leu Gly Arg Leu Phe Pro Glu Lys Ala Leu Thr
            500                 505                 510
Leu Pro Gly
        515

<210> SEQ ID NO 17
<211> LENGTH: 4
<212> TYPE: PRT
<213> ORGANISM: Artificial Sequence
<220> FEATURE:
<223> OTHER INFORMATION: stromal targeting domain
<220> FEATURE:
<221> NAME/KEY: VARIANT
<222> LOCATION: 1
<223> OTHER INFORMATION: Xaa = Ile or Val
<220> FEATURE:
<221> NAME/KEY: VARIANT
<222> LOCATION: 2
<223> OTHER INFORMATION: Xaa = any amino acid
<220> FEATURE:
<221> NAME/KEY: VARIANT
<222> LOCATION: 3
<223> OTHER INFORMATION: Xaa = Ala or Cys

<400> SEQUENCE: 17

Xaa Xaa Xaa Ala
 1

<210> SEQ ID NO 18
<211> LENGTH: 3
<212> TYPE: PRT
<213> ORGANISM: Artificial Sequence
```

-continued

```
<220> FEATURE:
<223> OTHER INFORMATION: linker sequence

<400> SEQUENCE: 18

Gly Ser Gly
 1
```

1

CHLAMYDOMONAS EPSPS CHLOROPLAST TRANSIT PEPTIDE (CTP) AND EXPRESSION CASSETTES AND TRANSGENIC PLANTS UTILIZING THE CTP

CROSS REFERENCE TO RELATED APPLICATIONS

This is a utility application which claims the benefit of U.S. Provisional Patent Application No. 61/095,134, filed Sep. 8, 2008, which is hereby incorporated in its entirety by reference herein.

REFERENCE TO SEQUENCE LISTING SUBMITTED ELECTRONICALLY

The official copy of the sequence listing is submitted electronically via EFS-Web as an ASCII formatted sequence listing with a file named "377480_SequenceListing.txt", created on Sep. 1, 2009, and having a size of 34 kilobytes and is filed concurrently with the specification. The sequence listing contained in this ASCII formatted document is part of the specification and is herein incorporated by reference in its entirety.

FIELD OF THE INVENTION

The present invention relates to the field of plant molecular biology, more particularly to the identification and use of regulatory elements in plants.

BACKGROUND OF THE INVENTION

Chloroplast biogenesis in plants is dependent upon the coordinated activities of two independent genetic systems localized in the chloroplast and the nucleus (see Cline and Henry (1996), Annu. Rev. Cell Dev. Biol. 12, 1-26). The vast constituent chloroplast proteins are encoded by the nuclear genes and are synthesized cytoplasmically- as precursor forms which contain N-terminal extensions known as transit peptides. The transit peptide is instrumental for specific recognition of the chloroplast surface and in mediating the post-translational translocation of pre-proteins across the chloroplast envelope and thence to the various different subcompartments within the chloroplast (e.g. stroma, thylakoid and thylakoid membrane).

Genes reported to have naturally encoded transit peptide sequences at their N-terminus include the chloroplast small subunit of ribulose-1,5-bisphosphate carboxylase (RuBisCo), de Castro Silva Filho et al. (1996) Plant Mol. Biol. 30: 769-780; Schnell, D. J. et al. (1991) J. Biol. Chem. 266 (5): 3335-3342; 5-(enolpyruvyl) shikimate-3-phosphate synthase (EPSPS), Archer et al. (1990) J. Bioenerg. and Biomemb. 22 (6):789-810; tryptophan synthase. Zhao, J. et al. (1995) J. Biol. Chem. 2 70 (11):6081-6087; plastocyanin, Lawrence et al. (1997) J. Biol. Chem. 272 (33):20357-20363; chorismate synthase, Schmidt et al. (1993) J. Biol. Chem. 268 (36):27477-27457; and the light harvesting chlorophyll a/b binding protein (LHBP), Lamppa et al. (1988) J. Biol. Chem. 263: 14996-14999, although not all of these sequences have been useful in the heterologous expression of chloroplast-targeted proteins in higher plants.

SUMMARY OF INVENTION

Compositions and methods for chloroplast targeting of polypeptides in a plant are provided. Compositions comprise expression cassettes comprising a nucleotide sequence encoding a chloroplast targeting peptide (or chloroplast transit peptide, "CTP") sequence derived from an algal organism operably linked to nucleotide sequence of interest. These expression constructs are useful for expression and proper targeting of the nucleotide sequence of interest in a monocot or a dicot plant. The invention further provides vectors comprising the expression cassettes, and plants and plant cells having stably incorporated or transiently expressed into their genomes an expression cassette described above. Additionally, compositions include transgenic seed of such plants.

Methods are also provided for expressing a nucleotide sequence in a plant or plant cell, as well as methods for identifying algal CTP sequences for use in a plant.

DETAILED DESCRIPTION

Figure 1:
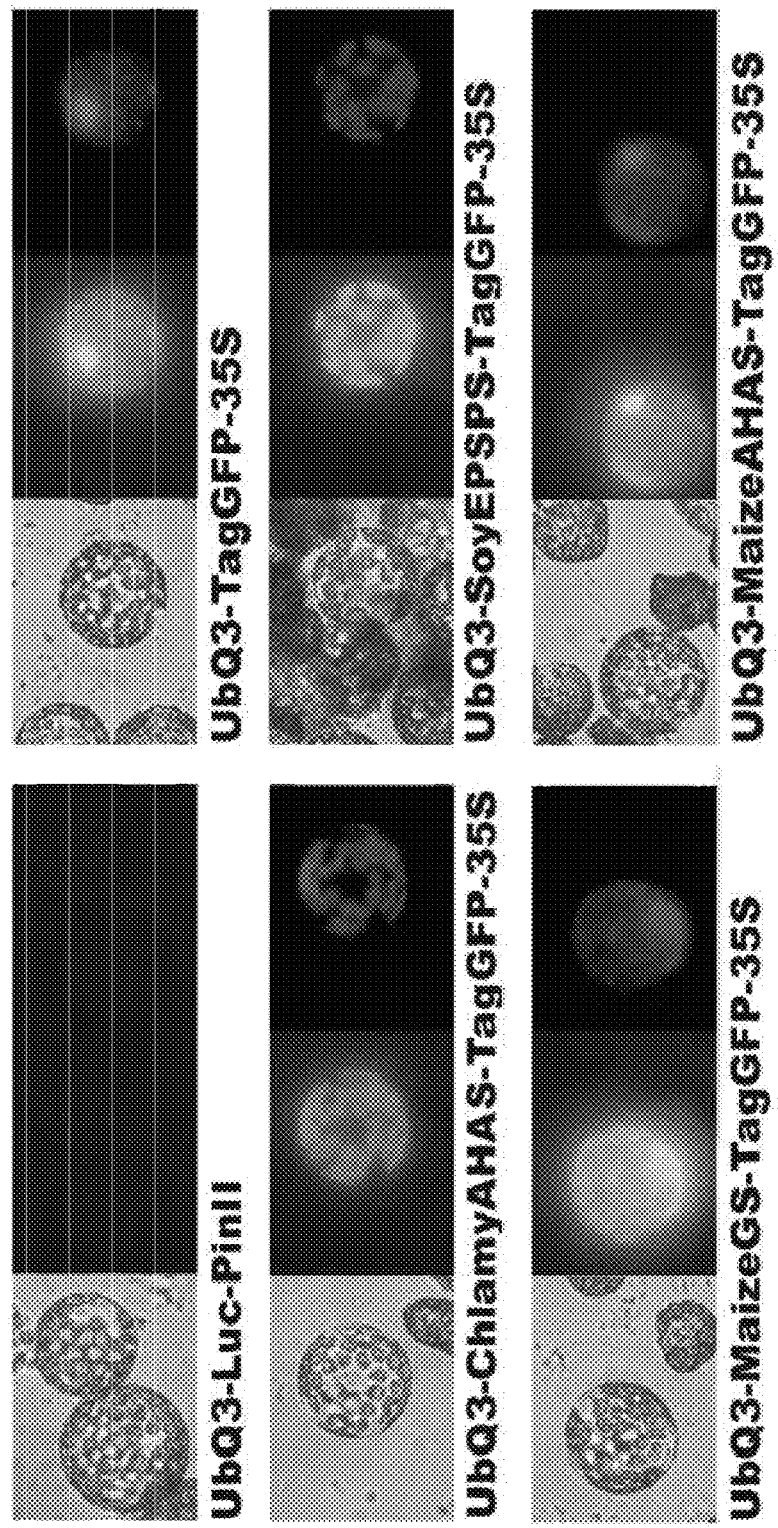
FIG. 1 demonstrates TagGFP expression in tobacco protoplasts.

In the production of transgenic plants it is often useful to direct foreign proteins to specific subcellular locations, e.g., the chloroplast, vacuole, mitochondria, or ER. Previous workers have fused DNA sequences encoding transit peptides from various plant genes to the genes of interest. When the gene is translated the resulting protein has the plant transit peptide fused to the amino terminus of the protein of interest, and thus the protein is directed, with varying efficiency, to the desired subcellular compartment.

Thus, the present invention is drawn to compositions and methods for chloroplast targeting of polypeptides in higher plants or plant cells. The compositions of the present invention comprise expression cassettes comprising a nucleotide sequence encoding a chloroplast transit peptide (CTP) derived from an algal organism operably linked to a nucleotide sequence of interest. In one embodiment, the CTP is derived from *Chlamydomonas* sp. In another embodiment, the CTP comprises the amino acid sequence set forth in SEQ ID NO:3, 5, or 7 or an amino acid sequence encoded by SEQ ID NO:1, 2, 4, or 6, as well as variants, fragments, and derivatives thereof. In addition, transformed plants, plant cells, and seeds are provided.

The CTP-encoding sequences of the invention, when assembled within a DNA construct such that the CTP-encoding sequence is operably linked to a nucleotide sequence of interest, facilitate co-translational or post-translational transport of the peptide of interest to the chloroplast of a plant cell stably transformed with this DNA construct. Methods for expressing a nucleotide sequence in a plant comprise introducing into plant cells an expression cassette comprising a CTP-encoding nucleotide sequence of the invention operably-linked to a nucleotide sequence of interest, and regenerating a transformed plant from the plant cell.

The articles "a" and "an" are used herein to refer to one or more than one (i.e., to at least one) of the grammatical object of the article. By way of example, "an element" means one or more elements.

As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Chloroplast Transit Peptides

Chloroplasts are organelles found in plant cells and eukaryotic algae that conduct photosynthesis. The chloroplast is a complex cellular organelle composed of three membranes: the inner envelope membrane, the outer envelope membrane, and the thylakoid membrane. The membranes together enclose three aqueous compartments termed the intermediate space, the stroma, and the thylakoid lumen. While chloroplasts contain their own circular genome, many constituent chloroplast proteins are encoded by the nuclear genes and are cytoplasmically-synthesized as precursor forms which contain N-terminal extensions known as chloroplast transit peptides (CTPs). The CTP is instrumental for specific recognition of the chloroplast surface and in mediating the post-translational translocation of pre-proteins across the chloroplast envelope and into the various different subcompartments within the chloroplast (e.g. stroma, thylakoid and thylakoid membrane).

At least two distinct functional domains have been identified in chloroplast transit peptides: the stromal targeting domain (STD) and the lumen targeting domain (LTD). STDs govern access to the general import pathway and are both necessary and sufficient for import of the passenger protein to the stroma. Stromal protein precursors possess transit peptides that contain only an STD, whereas thylakoid lumenal protein precursors have both an STD and an LTD.

STDs range in length from about 30 to 120 residues and are rich in hydroxylated residues and deficient in acidic residues. They tend to share several compositional motifs: an amino terminal 10-15 residues devoid of Gly, Pro and charged residues; a variable middle region rich in Ser, Thr, Lys and Arg; and a carboxy-proximal region with loosely conserved sequence (Ile/Val-X-Ala/Cys-Ala; SEQ ID NO:17) for proteolytic processing. However, there are no extensive blocks of sequence conservation, nor any conserved secondary structural motifs. Theoretical analyses suggest that STDs adopt predominantly random coil conformations.

Genes reported to have naturally encoded transit peptide sequences at their N-terminus include the chloroplast small subunit of ribulose-1,5-bisphosphate carboxylase (RuBisCo), de Castro Silva Filho et al. (1996) Plant Mol. Biol. 30: 769- 780; Schnell, D. J. et al. (1991) J. Biol. Chem. 266 (5): 3335-3342; 5-(enolpyruvyl) shikimate-3-phosphate synthase (EPSPS), Archer et al. (1990) J. Bioenerg. and Biomemb. 22 (6):789-810; tryptophan synthase. Zhao, J. et al. (1995) J. Biol. Chem. 2 70 (11):6081-6087; plastocyanin, Lawrence et al. (1997) J. Biol. Chem. 272 (33):20357-20363; chorismate synthase, Schmidt et al. (1993) J. Biol. Chem. 268 (36):27477-27457; and the light harvesting chlorophyll a/b binding protein (LHBP), Lamppa et al. (1988) J. Biol. Chem. 263: 14996-14999. Although several CTPS have been described, only a few have been utilized successfully in attempts to target chimeric molecules to chloroplasts in higher plants.

The present invention discloses the use of CTPs derived from algal species, particularly *Chlamydomonas* sp., in higher plants. For the purposes of the present invention, "higher plants" are considered members of the subkingdom Embryophytae. In one embodiment, the CTP useful in the methods and compositions disclosed herein is derived from *Chlamydomonas*. In another embodiment, the CTP is set forth in SEQ ID NO:3, 5, or 7, or is encoded by SEQ ID NO:1, 2, 4, or 6, including variants, fragments, and derivatives thereof. However, one of skill in the art would understand how to identify chloroplast transit peptides other than the ones disclosed herein. For example, a number of CTPs (or protein sequences comprising CTPs) are listed in GEN-BANK®.

The CTPs disclosed herein are useful for targeting a polypeptide to the chloroplast of a plant cell. In one embodiment, the CTPs disclosed herein provide improved translocation compared to CTPs derived from, for example, higher plant organisms. The CTPs disclosed herein may result in an at least about 20%, at least about 30%, at least about 40%, at least about 50%, at least about 60%, at least about 70%, at least about 80%, at least about 90%, at least about 100%, or greater, or at least about 2-fold, at least about 3-fold, at least about 4-fold, or greater improvement in translocation of the polypeptide into the chloroplast when compared to a reference CTP. An improvement can be measured in terms of the amount of polypeptide that gets translocated into the chloroplast, the amount of active polypeptide that gets translocated into the chloroplast, or both. An improvement can also be measured in terms of an improvement in the phenotype of an organism transformed with the chloroplast-targeted protein of interest. For example, where the CTP of the invention is used to target an herbicide resistance protein to the chloroplast of the plant, an improvement in activity can be measured in terms of an improvement in herbicide resistance.

Expression Cassettes

The CTP-encoding sequences of the invention may be provided in an expression cassette that allows it to drive expression and localization of a polypeptide encoded by the nucleotide sequence of interest into the chloroplast of plant cells. By "expression cassette" is intended a DNA construct that is capable of resulting in the expression of a protein from an open reading frame in a cell. The cassette will include in the 5 –3 direction of transcription, a transcriptional initiation region preferably comprising a promoter suitable for expression in a plant cell of interest, operably-linked to a CTP-encoding sequence of the invention, which is further operably linked to a nucleotide sequence of interest, and a translational and transcriptional termination region (i.e., termination region) functional in plants. The CTP-encoding nucleotide sequence and the nucleotide sequence of interest may be separated from one another by nucleotide sequences encoding one or more "linker" amino acids as discussed elsewhere herein.

The cassette may additionally contain at least one additional gene to be cotransformed into the organism, such as a selectable marker gene. Alternatively, the additional gene(s) can be provided on multiple expression cassettes. Such an expression cassette is provided with a plurality of restriction sites for insertion of the nucleotide sequence of interest to be under the transcriptional regulation of the regulatory regions.

The expression cassette may further comprise 3 and/or 5 untranslated region(s). By "3 untranslated region" is intended a nucleotide sequence located downstream of a coding sequence. Polyadenylation signal sequences and other sequences encoding regulatory signals capable of affecting the addition of polyadenylic acid tracts to the 3 end of the mRNA precursor are 3 untranslated regions. By "5 untranslated region" is intended a nucleotide sequence located upstream of a coding sequence. Other upstream or downstream untranslated elements include enhancers. Enhancers are nucleotide sequences that act to increase the expression of a promoter region. Enhancers are well known in the art and include, but are not limited to, the SV40 enhancer region and the 35S enhancer element.

The termination region may be native with the CTP-encoding nucleotide sequence of the present invention, may be native with the nucleotide sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

The expression cassettes described herein may further comprise one or more regulatory elements other than CTP, as well as additional CTPs known in the art. By "regulatory element" or "regulatory region" is intended a portion of nucleic acid found upstream or downstream of a gene, that may be comprised of either DNA or RNA, or both DNA and RNA and that is involved in gene expression. Regulatory elements may be capable of mediating organ specificity, or controlling developmental or temporal gene activation and include promoter elements, core promoter elements, elements that are inducible in response to an external stimulus, elements that are activated constitutively, transcriptional terminators, polyadenylation signals, and elements that decrease or increase promoter activity such as negative regulatory elements or transcriptional enhancers, respectively. By "cis-acting" is intended a sequence that is physically contiguous with the transcribed sequence. Cis-acting sequences typically interact with proteins or other molecules to carry out (turn on/off, regulate, modulate, etc.) transcription. By "transcriptional enhancer" is intended a nucleic acid sequence that, when positioned proximate to a promoter and present in a transcription medium capable of supporting transcription, confers increased transcription activity compared to that resulting from the promoter in the absence of the enhancer. Enhancers may function upstream, within, or downstream of a gene, even as far away as 50 kilobases from the transcriptional initiation site. Enhancers may also function independently of their orientation. By "transcriptional terminator" is intended a DNA sequence that includes a nucleotide base pair sequence necessary for reducing or eliminating transcription. By "polyadenylation signal" is intended a sequence that controls the termination of transcription and translation.

In one aspect of the invention, synthetic DNA sequences are designed for a given polypeptide, such as the chloroplast-targeted polypeptides useful in the methods disclosed herein. Expression of the open reading frame of the synthetic DNA sequence in a cell results in production of the polypeptide. Synthetic DNA sequences can be useful to simply remove unwanted restriction endonuclease recognition sites, to facilitate DNA cloning strategies, to alter or remove any potential codon bias, to alter or improve GC content, to remove or alter alternate reading frames, and/or to alter or remove intron/exon splice recognition sites, polyadenylation sites, Shine-Delgarno sequences, unwanted promoter elements and the like that may be present in a native DNA sequence. It is also possible that synthetic DNA sequences may be utilized to introduce other improvements to a DNA sequence, such as introduction of an intron sequence, creation of a DNA sequence that in expressed as a protein fusion to organelle targeting sequences, such as chloroplast transit peptides, apoplast/vacuolar targeting peptides, or peptide sequences that result in retention of the resulting peptide in the endoplasmic reticulum. Synthetic genes can also be synthesized using host cell-preferred codons for improved expression, or may be synthesized using codons at a host-preferred codon usage frequency. See, for example, Campbell and Gowri (1990) *Plant Physiol.* 92:1-11; U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

The nucleic acids of interest to be targeted to the chloroplast may also be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Variants and Fragments

Nucleic acid molecules that are fragments of the disclosed CTP sequences are also encompassed by the present invention. By "fragment" is intended a portion of the CTP sequence. A fragment of a nucleotide sequence may be biologically active and hence be capable of facilitating the translocation of a polypeptide of interest into the chloroplast of a plant, or it may be a fragment that can be used as a hybridization probe or PCR primer using methods disclosed below. Assays to determine whether such fragments have CTP activity are well known in the art.

Nucleic acid molecules that are fragments of a CTP-encoding nucleotide sequence disclosed herein may comprise at least about 90, 100, 125, 150, 175, 200, 225, 250, 275, 300, contiguous nucleotides, or up to the number of nucleotides present in a full-length CTP sequence disclosed herein (for example, 306 nucleotides for SEQ ID NO:1) depending upon the intended use. By "contiguous" nucleotides is intended nucleic acid residues that are immediately adjacent to one another. Biologically active fragments of the CTP-encoding sequences of the present invention will encode a CTP that retains activity. By "retains CTP activity" is intended that the fragment will direct the translocation into the chloroplast of at least about 30%, at least about 50%, at least about 70%, or at least about 80% of the polypeptide encoded by the nucleotide sequence of interest. In one embodiment, a fragment of a CTP-encoding nucleotide sequence disclosed herein may comprise one or more deletions of SEQ ID NO:1, 2, 4, or 6, including up to about 2, about 3, about 4, about 5, about 6, about 7, about 8, about 9, about 10, about 12, about 15, about 18, about 21, about 24, about 27, about 30 or more deletions. In another embodiment, a fragment of a CTP-encoding nucleotide sequence disclosed herein may encode an amino acid comprising one or more deletions of SEQ ID NO:3, 5, or 7, including up to about 2, about 3, about 4, about 5, about 6, about 7, about 8, about 9, about 10 or more amino acid deletions.

A biologically active portion of a CTP can be prepared by isolating a portion of one of the CTP sequences of the invention and assessing the activity of that portion of the CTP. Methods for measuring CTP activity are well known in the art. See the section entitled "Evaluation of CTP Activity" for examples of suitable methods.

Variants of the CTP-encoding nucleotide sequences or the CTP amino acid sequences disclosed herein are also encompassed. By "variant" is intended a sufficiently identical sequence, or a sequence that differs by at least one amino acid from a native chloroplast transit peptide. CTP-encoding sequences encompassed by the present invention are sufficiently identical to the nucleotide sequence of SEQ ID NO:1, 2, 4, or 6. CTP sequences encompassed herein are sufficiently identical to the amino acid sequence of SEQ ID NO:3, 5, or 7. By "sufficiently identical" is intended a nucleotide sequence that has at least about 70% or 75%, about 80% or 85% sequence identity, about 90%, 91%, 92%, 93%, 94%, 95%, 96%, 97%, 98% or 99% sequence identity compared to a reference sequence using one of the alignment programs as described herein.

In one embodiment, the variants disclosed herein include nucleotide or amino acid substitutions, deletions, truncations, and insertions of one or more nucleotides of SEQ ID NO:1, 2, 4, or 6, or one or more amino acids of SEQ ID NO:3, 5, or 7, including up to about 2, about 3, about 4, about 5, about 6, about 7, about 8, about 9, about 10, about 15, about 20, about 25, about 30 or more amino acid substitutions, deletions or insertions.

Naturally occurring variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still have CTP activity as defined herein.

Variants encompassed by the present invention are biologically active, that is they continue to possess the desired biological activity of the native sequence, that is, retaining CTP activity (i.e., facilitating translocation of the expressed polypeptide to the chloroplast). By "retains CTP activity" is intended that the variant will direct the translocation to the chloroplast of at least about 30%, at least about 50%, at least about 70%, or at least about 80% of the polypeptide encoded by the nucleotide sequence of interest. Methods for measuring CTP activity are well known in the art. See the section entitled "Evaluation of CTP Activity" for examples of suitable methods.

The skilled artisan will further appreciate that changes to the CTP can be introduced by mutation into the nucleotide sequence encoding the CTPs of the invention without altering the ability of the CTP to drive translocation of a polypeptide in the chloroplast of a plant cell. Thus, variant isolated nucleic acid molecules can be created by introducing one or more nucleotide substitutions, additions, or deletions into the corresponding nucleotide sequence disclosed herein. Mutations can be introduced by standard techniques, such as site-directed mutagenesis and PCR-mediated mutagenesis. Such variant nucleotide sequences are also encompassed by the present invention.

Alternatively, variant nucleotide sequences can be made by introducing mutations randomly along all or part of the CTP sequence, such as by saturation mutagenesis, and the resultant mutants can be screened for ability to drive translocation of an operably linked polypeptide sequence into the chloroplast a plant cell.

By "operably linked" is intended a functional linkage between a regulatory element (e.g., a CTP) and a second sequence, wherein the CTP sequence directs the translocation of the polypeptide of interest to the chloroplast of a plant cell. Generally, but not always, operably linked means that the nucleic acid sequences being linked are contiguous and, where necessary to join two protein coding regions, contiguous and in the same reading frame.

To determine the percent identity of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the comparison is across the entirety of the reference sequence (e.g., SEQ ID NO:1, 2, 4, or 6). The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN program of Altschul et al. (1990) *J. Mol. Biol.* 215:403. BLAST nucleotide searches can be performed with the BLASTN program, score=100, wordlength=12, to obtain nucleotide sequences homologous to sequences of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTN) can be used. See, www.ncbi.nlm.nih.gov. Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the DNA sequence, and thus can provide data about the sequence conservation of the entire nucleotide sequence. The ClustalW algorithm is used in several commercially available DNA analysis software packages, such as the ALIGNX module of the vector NTi Program Suite (Informax, Inc). A non-limiting example of a software program useful for analysis of ClustalW alignments is GeneDoc™. Genedoc™ (Karl Nicholas) allows assessment of DNA similarity and identity between multiple genes. Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package (available from Accelrys, Inc., 9865 Scranton Rd., San Diego, Calif., USA).

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

Using methods such as PCR, hybridization, and the like, corresponding sequences from other organisms, particularly other algal organisms, can be identified, such sequences having substantial identity to the sequences of the invention. See, for example, Sambrook J., and Russell, D. W. (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY). Sequences identified by their identity to the CTP sequences set forth herein are encompassed by the present invention.

In another embodiment, CTPs can be identified based on the identification of sequences known to comprise CTPs. For example, chloroplast-targeted sequences can be identified based on similarity to the chloroplast-targeted proteins disclosed herein or known in the art (e.g., acetolactate synthase (AHAS), small subunit (SSU), and EPSPS). The CTP sequence from these targeted proteins can be identified using methods known in the art. See, for example, Emanuelsson and von Heijne (2001) Biochimica et Biophysica Acta 1541:114-119; Nielson et al. (1997) Protein Eng. 10:1-6; and, Nielson and Krogh (1998) Intell. Syst. Mol. Biol. 6:122-130, each of which is herein incorporated by reference in its entirety. A variety of computer programs are also available for identifying. See, for example, ChloroP (which can be found at the internet address cbs.dtu.dk/services/ChloroP); Predotar (which can be found at the internet address inra.fr/Internet/Produits/Predotar); and, SignalP (which can be found at the internet address cbs.dtu.dk/services/SignalP).

Oligonucleotide primers can be designed for use in PCR reactions to amplify corresponding DNA sequences from cDNA or genomic DNA from an organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Cold Spring Harbor, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, and partially-mismatched primers.

In a hybridization method, all or part of a known nucleotide sequence can be used to screen cDNA or genomic libraries. Methods for construction of such cDNA and genomic libraries are generally known in the art and are disclosed in Sambrook and Russell, 2001, supra. The hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known CTP-encoding sequence disclosed herein or primers to the known chloroplast targeted protein. Degenerate primers designed on the basis of conserved nucleotides in the nucleotide sequence can additionally be used. The probe typically comprises a region of nucleotide sequence that hybridizes under stringent conditions to at least about 12, at least about 20, at least about 25, 30, 35, 40, 45, 50, 55, 60, 75, 100, 125, 150, 175, 200, 250, 300, 350, or 400 consecutive nucleotides of the CTP-encoding sequence of the invention, a nucleotide sequence encoding a chloroplast targeted protein, or a fragment or variant thereof. Preparation of probes for hybridization is generally known in the art and is disclosed in Sambrook and Russell, 2001, supra, herein incorporated by reference.

For example, the entire CTP-encoding sequence disclosed herein (or coding sequence for chloroplast-targeted protein), or one or more portions thereof, may be used as a probe capable of specifically hybridizing to corresponding CTP-like sequences. To achieve specific hybridization under a variety of conditions, such probes include sequences that are unique and are at least about 10 nucleotides in length, or at least about 20 nucleotides in length. Such probes may be used to amplify corresponding CTP-encoding sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, or less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. Optionally, wash buffers may comprise about 0.1% to about 1% SDS.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), the SSC concentration can be increased so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated sequences that have CTP activity and which hybridize under stringent conditions to the CTP sequences disclosed herein, or to fragments thereof, are encompassed by the present invention.

Methods of Use

Methods of the present invention are directed to the proper expression, translocation, and processing of chloroplast-targeted sequences in higher plants and plant cells under the control of the CTP sequences of the present invention. For the purposes of the present invention, a "processed" chloroplast targeted protein is one in which the CTP has been removed. At the time of translocation of a chloroplast targeted protein into the chloroplast of a plant cell, the CTP is removed from targeted protein by cleavage at a particular "cleavage site" between the CTP and the mature protein. The cleavage site can be determined experimentally, or may be predicted based on sequence structure (e.g., by alignment of the unprocessed protein with chloroplast targeted proteins in which the cleavage site is known, by analyzing the sequence for the presence of characteristic CTP domains, and the like) or by using one or more algorithms for cleavage site prediction as discussed elsewhere herein (e.g., SignalP).

The transgenic plants may have a change in phenotype, including, but not limited to, an altered pathogen or insect defense mechanism, an increased resistance to one or more herbicides, an increased ability to withstand stressful environmental conditions, a modified ability to produce starch, a modified level of starch production, a modified oil content and/or composition, a modified ability to utilize, partition and/or store nitrogen, and the like. These results can be achieved through the expression and targeting of a polypeptide of interest to chloroplasts in plants, wherein the polypeptide of interest functions in the chloroplast. The CTP sequences of the invention are useful for targeting native sequences as well as heterologous (non-native) sequences in higher plants. For the purposes of the present invention, "higher plants" are considered members of the subkingdom Embryophytae. In one embodiment, the plant is a monocotyledon. In another embodiment, the plant is a dicotyledon.

Generally, the nucleotide sequence encoding the CTP of the invention is provided in an expression cassette with a nucleotide sequence of interest for expression in the plant of interest. In one embodiment, the CTP-encoding sequences of the invention are useful for the improved translocation of native sequences in a plant. In other embodiments, the CTP-encoding sequences are useful for expression and translocation of polypeptides encoded by heterologous nucleotide sequences. By "heterologous nucleotide sequence" is intended a sequence that is not naturally operably-linked with the CTP-encoding sequence of the invention, including non-naturally occurring multiple copies of a naturally occurring DNA sequence. While this nucleotide sequence is heterologous to the CTP-encoding sequence, it may be homologous, or "native," or heterologous, or "foreign," to the plant host. In some cases, the transformed plant may have a change in phenotype. "Heterologous" generally refers to the nucleic acid sequences that are not endogenous to the cell or part of the native genome in which they are present, and have been added to the cell by infection, transfection, microinjection, electroporation, microprojection, or the like.

Any nucleotide sequence of interest may be used with the CTP-encoding sequences of the invention, so long as the polypeptide encoded by the nucleotide sequence of interest (i.e., the "polypeptide of interest") is functional in a chloroplast. Such nucleotide sequences include, but are not limited to, herbicide-tolerance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, and oil content and/or composition. More specific genes of interest for the present invention include, but are not limited to, genes that improve crop yield, genes that improve desirability of crops, genes encoding proteins conferring resistance to abiotic stress, such as drought, temperature, salinity, toxic metals or trace elements, or those conferring resistance to toxins such as pesticides and herbicides, or to biotic stress, such as attacks by fungi, viruses, bacteria, insects, and nematodes, and development of diseases associated with these organisms. It is recognized that any gene of interest can be operably linked to the CTP-encoding sequences of the invention and expressed in a plant, so long as the polypeptide encoded by the gene is functional in chloroplasts.

These nucleotide sequences of interest may encode proteins involved in providing disease or pest resistance. By "disease resistance" or "pest resistance" is intended that the plants avoid the harmful symptoms that are the outcome of the plant-pathogen interactions. Disease resistance and insect resistance genes such as lysozymes or cecropins for antibacterial protection, or proteins such as defensins, glucanases or chitinases for antifungal protection, or Bacillus thuringiensis endotoxins, protease inhibitors, collagenases, lectins, or glycosidases for controlling nematodes or insects are all examples of useful gene products. Examples of genes of interest may be found, for example, at www.nbiap.vt.edu/cfdocs/fieldtests2.cfm.

"Pest" includes, but is not limited to, insects, fungi, bacteria, viruses, nematodes, mites, ticks, and the like. Insect pests include insects selected from the orders *Coleoptera, Diptera,*

*Hymenoptera, Lepidoptera, Mallophaga, Homoptera, Hemiptera, Orthroptera, Thysanoptera, Dermaptera, Isoptera, Anoplura, Siphonaptera, Trichoptera*, etc., particularly *Coleoptera, Lepidoptera*, and *Diptera*. Viruses include but are not limited to tobacco or cucumber mosaic virus, ringspot virus, necrosis virus, maize dwarf mosaic virus, etc. Nematodes include but are not limited to parasitic nematodes such as root knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include but are not limited to *Pratylenchus* spp. Fungal pests include those that cause leaf, yellow, stripe and stem rusts.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS), in particular the sulfonylurea-type herbicides, genes coding for resistance to herbicides that act to inhibit the action of glutamine synthase, such as phosphinothricin or basta (e.g., the bar gene), glyphosate (e.g., the EPSP synthase gene and the GAT gene) or other such genes known in the art.

Genes that improve crop yield include dwarfing genes, such as Rht1 and Rht2 (Peng et al. (1999) *Nature* 400:256-261), and those that increase plant growth, such as ammonium-inducible glutamate dehydrogenase. Genes that improve desirability of crops include, for example, those that allow plants to have a reduced saturated fat content, those that boost the nutritional value of plants, and those that increase grain protein. Genes that improve salt tolerance are those that increase or allow plant growth in an environment of higher salinity than the native environment of the plant into which the salt-tolerant gene(s) has been introduced.

Plant Transformation Vectors

Typically the plant expression cassette will be inserted into a "plant transformation vector." By "transformation vector" is intended a DNA molecule that is necessary for efficient transformation of a cell. Such a molecule may consist of one or more expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. By "introducing" is intended to present to the organism being transformed the nucleotide construct in such a manner that the construct gains access to the interior of at least one cell of the organism.

This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as 'binary vectors'. Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication.

The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as in understood in the art (Hellens and Mullineaux (2000) *Trends in Plant Science,* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

Transformation of plant cells can be accomplished by one of several techniques known in the art. By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen). "Transgenic plants" or "transformed plants" or "stably transformed" plants or cells or tissues refer to plants that have incorporated or integrated exogenous nucleic acid sequences or DNA fragments into the plant cell. By "stable transformation" is intended that the nucleotide construct introduced into a plant integrates into the genome of the plant and is capable of being inherited by progeny thereof.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grow into mature plant and produce fertile seeds (e.g. Hiei et al. (1994) *The Plant Journal* 6:271-282; Ishida et al. (1996) *Nature Biotechnology* 14:745-750). A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods may be used to confirm the presence of the integrated heterologous gene of interest in the genome of transgenic plant.

Generation of transgenic plants may be performed by one of several methods, including, but not limited to, introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Plants

The present invention may be used for transformation of any higher plant species, including, but not limited to, monocots and dicots. In one embodiment, the CTP encompassed herein is active in both monocots and dicots. In another embodiment, the CTP is active only in monocots or only in dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

This invention is particularly suitable for any member of the monocot plant family including, but not limited to, maize, rice, barley, oats, wheat, sorghum, rye, sugarcane, pineapple, yams, onion, banana, coconut, and dates.

Evaluation of Plant Transformation

Following introduction of heterologous foreign DNA into plant cells, the transformation or integration of heterologous DNA in the plant genome is confirmed by various methods such as analysis of nucleic acids or proteins and metabolites associated with the integrated DNA.

PCR analysis is a rapid method to screen transformed cells, tissue or shoots for the presence of incorporated DNA at the earlier stage before transplanting into the soil (Sambrook and Russell, 2001. *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" then is probed with, for example, radiolabeled $^{32}$P target DNA fragment to confirm the integration of introduced DNA in the plant genome according to standard techniques (Sambrook and Russell, 2001, supra).

In Northern blot analysis, RNA is isolated from specific tissues of transformant, fractionated in a formaldehyde agarose gel, blotted onto a nylon filter according to standard procedures that are routinely used in the art (Sambrook and Russell, 2001, supra). Expression of RNA encoded by a heterologous gene operably linked to the CTP-encoding sequence is then tested by hybridizing the filter to a radioactive probe derived from the heterologous gene, by methods known in the art (Sambrook and Russell, 2001, supra).

Evaluation of CTP Activity

Assays to determine the efficiency by which the CTP sequences of the invention target a protein of interest to a chloroplast are known. See, for example, Mishkind et al. (1985) *J of Cell Biol* 100:226-234, which is herein incorporated by reference in its entirety. A reporter gene such as-glucuronidase (GUS), chloramphenicol acetyl transferase (CAT), or green fluorescent protein (GFP) is operably linked to the CTP sequence. This fusion is placed behind the control of a suitable promoter, ligated into a transformation vector, and transformed into a plant or plant cell. Following an adequate period of time for expression and localization into the chloroplast, the chloroplast fraction is extracted and reporter activity assayed. The ability of the isolated sequences to target and deliver the reporter protein to the chloroplast can be compared to other known CTP sequences. See de Castro Silva Filho et al. (1996) Plant Mol. Biol. 30: 769-780. Protein import can also be verified in vitro through the addition of proteases to the isolated chloroplast fraction. Proteins which were successfully imported into the chloroplast are resistant to the externally added proteases whereas proteins that remain in the cytosol are susceptible to digestion. Protein import can also be verified by the presence of functional protein in the chloroplast using standard molecular techniques for detection, or by evaluating the phenotype resulting from expression of a chloroplast targeted protein.

The following examples are offered by way of illustration and not by way of limitation.

EXPERIMENTAL

Example 1

*Chlamydomonas* AHAS CTP

The *Chlamydomonas* AHAS CTP (SEQ ID NO:3) was identified from comparison of the full-length *Chlamydomonas* AHAS ("ChlamyAHAS") peptide (GENBANK accession AF022816; SEQ ID NO:8) with several AHAS peptides from plants, bacteria, yeast and fungi. This alignment shows that the ChlamyAHAS CTP shows very little sequence conservation with plant CTPs, whereas the mature proteins show conserved elements. Thus, by comparing the multiple AHAS proteins with the ChlamyAHAS protein, it was inferred that amino acids 1-99 of the *Chlamydomonas* AHAS protein comprised the CTP. The predicted processing site for this CTP upon import into the *Chlamydomonas* chloroplast is at approximately amino acid 92 of SEQ ID NO:8.

Example 2

*Chlamydomonas* RuBisCo Small Subunit (SSU) CTP

The *Chlamydomonas* SSU CTP (SEQ ID NO:5) was identified from comparison of the full-length *Chlamydomonas* SSU ("ChlamySSU") peptide (GENBANK accession CAA28160; SEQ ID NO:9) with several plant RuBisCo small subunit peptides. This alignment shows that the ChlamySSU CTP shows very little sequence conservation with plant CTPs, whereas the mature proteins show conserved elements. Thus, by comparing the known processing sites of several plant RuBisCo proteins with the ChlamySSU protein, it was inferred that amino acids 1-45 of the *Chlamydomonas* SSU protein (SEQ ID NO:9) comprised the CTP.

The cleavage site for the *Chlamydomonas* RuBisCO small subunit precursor ("ChlamySSU") has been determined empirically to be between residues 44 and 45 of SEQ ID NO:9 (Schmidt et al 1979, Journal of Cell Biology 83:615-662).

Example 3

*Chlamydomonas* EPSPS CTP

The *Chlamydomonas* EPSPS CTP (SEQ ID NO:7) was identified from comparison of the full-length *Chlamydomonas* EPSPS peptide (GENBANK accession XP_001702942; SEQ ID NO:10) with several plant and bacterial EPSPSs. This alignment showed that the ChlamyEPSPS CTP shows very little sequence conservation with plant CTPs, whereas the mature proteins show conserved elements. Thus, by comparing several EPSPS proteins with the ChlamyEPSPS protein, it was inferred that amino acids 1-75 of the *Chlamydomonas* EPSPS protein (SEQ ID NO:10) comprised the CTP. The predicted processing site for this CTP upon import into the *Chlamydomonas* chloroplast is at approximately amino acid 61 of SEQ ID NO:10.

TABLE 1

*Chlamydomonas* CTPs

| Protein | SEQ ID NO: | Residues of Precursor Protein Used for CTP | Predicted Cleavage Site |
|---|---|---|---|
| ChlamyAHAS | 8 | 1-99 | 92 |
| ChlamySSU | 9 | 1-45 | Amino Acid 44 or Amino Acid 45 |
| ChlamyEPSPS | 10 | 1-75 | 61 |

Example 4

DNA Constructs for Using the *Chlamydomonas* CTPs for Protein Targeting

A DNA element utilizing the *Chlamydomonas* CTP, including the *Chlamydomonas* AHAS, *Chlamydomonas* SSU, or *Chlamydomonas* EPSPS CTPs to generate multiple constructs for targeting of proteins to chloroplasts can involve inclusion of convenient restriction endonuclease recognition sites (for example a Bam HI restriction site) as well as small peptide linkers between the chloroplast CTP and the protein (for example a Gly-Ser-Gly tripeptide CTP; SEQ ID NO:18). Furthermore, such DNA elements can be designed and made synthetically, in a way that the DNA sequence is varied from the original DNA, but encodes the identical peptide.

Alternatively, one can design DNA constructs such that no restriction enzyme sites are needed, and the CTP/protein fusion can be accomplished by total synthesis of the combined coding region, or by PCR based strategies, including "sewing PCR" and the like.

One can also design the CTP/protein fusion in a manner where some of either protein is truncated. For example, one can remove one or more amino acids from the N-terminus of a bacterially expressed protein, and still achieve a functional fusion to a *Chlamydomonas* CTP.

A cassette containing a synthetically designed DNA sequence encoding the *Chlamydomonas* AHAS CTP that incorporates a BamHI restriction site and a Gly-Ser-Gly linker was designed. These DNA constructs contain (from 5' to 3') (1) a Pst I cloning site, (2) the bases ACC to provide "Kozak" context for efficient translation, (3) the portion of the gene encoding the amino terminal methionine through the known transit peptide cleavage site of the ChlamyAHAS, and including a small DNA region encoding the amino acids C-terminal to the cleavage site, (4) DNA bases encoding the residues Gly-Ser-Gly with an embedded BamH I cloning site, and, (5) the coding region of the gene of interest.

A cassette containing a synthetically designed DNA sequence encoding the *Chlamydomonas* SSU CTP that incorporates a BamHI restriction site and a Gly-Ser-Gly linker was designed. These DNA constructs contain (from 5' to 3') (1) a Pst I cloning site, (2) the bases ACC to provide "Kozak" context for efficient translation, (3) the portion of the gene encoding the amino terminal methionine through the known transit peptide cleavage site of the ChlamySSU, and including a small DNA region encoding the amino acids C-terminal to the cleavage site, (4) DNA bases encoding the residues Gly-Ser-Gly with an embedded BamH I cloning site, and, (5) the coding region of the gene of interest.

A cassette containing a synthetically designed DNA sequence encoding the *Chlamydomonas* EPSPS CTP that incorporates a BamHI restriction site and a Gly-Ser-Gly linker was designed. These DNA constructs contain (from 5' to 3') (1) a Pst I cloning site, (2) the bases ACC to provide "Kozak" context for efficient translation, (3) the portion of the gene encoding the amino terminal methionine through the known transit peptide cleavage site of the ChlamyEPSPS, and including a small DNA region encoding the amino acids C-terminal to the cleavage site, (4) DNA bases encoding the residues Gly-Ser-Gly with an embedded BamH I cloning site, and, (5) the coding region of the gene of interest.

Example 5

Fusion of a Transit Peptide from a Non-Plant Species to a Heterologous Protein, and Proper Localization and Cleavage in Monocots: *Chlamydomonas* AHAS CTP Functions in Monocots DNA constructs were designed such that the resulting protein encoded the *Chlamydomonas* AHAS transit peptide ("ChlamyAHAS") at the N-terminus, followed by a protein fusion to a gene conferring herbicide resistance upon cells (GRG-1; U.S. Pat. No. 7,405,347). For the ChlamyAHAS precursor, the transit peptide cleavage sites were inferred from alignments of the protein sequences to ALS proteins from bacteria, fungi and yeast.

These DNA constructs contain (from 5' to 3') a Pst I cloning site, (2) the bases ACC to provide "Kozak" context for efficient translation, (3) the portion of the gene encoding the amino terminal methionine through the known transit peptide cleavage site of the ChlamyAHAS CTP and including a small DNA region encoding the amino acids C-terminal to the cleavage site, (4) DNA bases encoding the residues Gly-Ser-Gly with an embedded BamH I cloning site, and, (5) the coding region of the gene of interest (in this case GRG-1).

These DNAs molecules were made synthetically (DNA 2.0 of Menlo Park, Calif.). The DNA sequence of the region containing this construct is provided as SEQ ID NO:11, and the resulting amino acid sequence is provided as SEQ ID NO:12.

A control construct (pAG250) was made, which contains GRG-1 expressed from the TrpPro5 promoter, wherein the GRG-1 protein does not have a chloroplast CTP.

This no CTP/GRG-1 construct was engineered into a vector for use in *Agrobacterium*-mediated transformation of maize embryos, and transgenic maize plants containing this construct were generated. To transformed plants were analyzed by PCR to confirm presence of the construct in the maize lines, and these $T_0$ plants were then out-crossed to a non-transgenic line to generate hemizygous $T_1$ progeny. The resulting $T_1$ transgenic plants produce large amounts of GRG-1 protein. Nonetheless, plants transformed with pAG250 and expressing unlocalized GRG-1 are not resistant to glyphosate.

The algal CTP ChlamyAHAS/GRG-1 construct was engineered into a vector for use in *Agrobacterium*-mediated transformation of maize embryos, and transgenic maize plants containing this construct were generated.

$T_0$ transformed plants were analyzed by PCR to confirm presence of the construct in the maize lines, and these $T_0$ plants were then out-crossed to a non-transgenic line to generate hemizygous $T_1$ progeny. The resulting $T_1$ transgenic plants are resistant to spray applications of glyphosate (as compared to non-transgenic controls).

Western blots of leaf tissue from transgenic maize plants show that these plants express the GRG-1 protein. Furthermore, the size of the protein identified by Western blot is consistent with import of the protein into chloroplasts, and processing of the ChlamyAHAS/GRG-1 protein at or near the cleavage site.

Thus the ChlamyAHAS CTP is sufficient to target GRG-1 to the maize chloroplast, and result in a phenotype (herbicide resistance) that is not conferred by GRG-1 in the absence of targeting to the chloroplast.

Example 6

Fusion of a Transit Peptide from a Non-Plant Species to a Heterologous Protein, and Proper Localization and Cleavage in Monocots: *Chlamydomonas* SSU CTP Functions in Monocots To test if an algal chloroplast CTP can function in monocots, transgenic monocot plants were generated and expression and cleavage of an algal CTP was assessed by Western blot analysis.

DNA constructs were designed such that the resulting protein encoded the algal transit peptide at the N-terminus, fused to a protein conferring herbicide resistance upon cells (in this case the GRG-8 protein; U.S. Patent Publication No. 20060150270)

These DNA constructs contain (from 5' to 3') (1) a Pst I cloning site, (2) the bases ACC to provide "Kozak" context for efficient translation, (3) the portion of the gene encoding the amino terminal methionine through the known transit peptide cleavage site of the ChlamySSU, and including a small DNA region encoding the amino acids C-terminal to the cleavage site, (4) DNA bases encoding the residues Gly-Ser- Gly with an embedded BamH I cloning site, and, (5) the coding region of the gene of interest (in this case GRG-8).

The DNA sequence of the region containing this construct is provided as SEQ ID NO:13, and the resulting amino acid sequence is provided as SEQ ID NO:14.

This CTP/GRG-8 construct (pAG1675) was engineered into a vector for use in *Agrobacterium*-mediated transformation of maize embryos, and transgenic maize plants generated and identified.

$T_0$ plants transformed with pAG1675 were analyzed by PCR to confirm presence of the construct in the maize lines, and these $T_0$ plants were then out-crossed to a non-transgenic line to generate hemizygous $T_1$ progeny. $T_1$ transgenic plants exhibited resistance to spray applications of glyphosate compared to non-transgenic controls.

Example 7

Expression and Processing of *Chlamydomonas* SSU Chloroplast CTP Fused to GRG-8 Protein in Maize Cells Western blots of leaf tissue from transgenic maize plants were found to express the CTP/GRG-8 protein. Total leaf protein was extracted from maize leaves (Pierce P-PER protein extract buffer) and separated on a 4-12% Bis-Tris gel. GRG-8 protein was visualized using goat anti-GRG8 polyclonal antibodies. A non-transgenic maize extract was compared alongside (lane 3). To evaluate CTP processing, a HIS-tagged GRG-8 protein standard was purified from an *E. coli* strain. The size of the protein identified by Western blot is consistent with import of the protein into chloroplasts, and processing of the CTP/GRG-8 protein within the ChlamySSU CTP, at or near the predicted cleavage site.

Example 8

Evaluation of Glyphosate Tolerance of Maize Plant Expressing *Chlamydomonas* SSU-GRG8 Protein The glyphosate spray tolerance of a transgenic maize event expressing the *Chlamydomonas* SSU-GRG8 protein was compared to several non-transgenic $T_0$ control plants. Individual plants were transferred to the greenhouse and grown in flats for 10 days. After 10 days, a glyphosate concentration that approximated a 1× field spray rate (7 mM supplemented with 0.1% Tween 20 as surfactant) was applied to the flats. The glyphosate was applied using a spray table to allow consistent application of the herbicide to individual plants. Plants were rated after 3 weeks to determine if the plants tolerated the glyphosate spray (mostly green leaf material: <50% damage) or did not tolerate the glyphosate spray (>75% damage, or plant death). The transgenic plant showed tolerance to glyphosate, whereas each of the control plants failed to show tolerance.

Example 9

Fusion of a Transit Peptide from a Non-Plant Species to a Heterologous Protein, and Proper Localization and Cleavage in Monocots: *Chlamydomonas* EPSPS CTP Functions in Monocots DNA and amino acid sequences for the *Chlamydomonas* EPSPS precursor were obtained from public databases. The transit peptide cleavage site was predicted based on alignments of the protein sequences with EPSPS proteins from bacteria, fungi and yeast. A synthetic gene was constructed which encoded the CTP from the amino terminal methionine through the predicted cleavage site. This DNA was ligated to create an in-frame fusion with the start codon of a synthetic GRG-23(ace3)(R173K) gene (U.S. Patent Application Publication No. 20080127372). This CTP-GRG-23(ace3)(R173K) cassette was then ligated into a plant transformation vector.

DNA constructs were designed such that the resulting protein encoded the *Chlamydomonas* EPSPS ("ChlamyEPSPS") transit peptide at the N-terminus, followed by fusion to a protein conferring herbicide resistance upon cells (GRG-23(ace3)(R173K)).

These DNAs molecules were made synthetically (DNA 2.0 of Menlo Park, Calif.). The DNA sequence of the region containing this construct is provided as SEQ ID NO:15, and the resulting amino acid sequence is provided as SEQ ID NO:16.

These DNA constructs contain (from 5' to 3'), (1) a Pst I cloning site, (2) the bases ACC to provide "Kozak" context for efficient translation, (3) the portion of the gene encoding the amino terminal methionine through the known transit peptide cleavage site of the ChlamyEPSPS and including a small DNA region encoding the amino acids C-terminal to the cleavage site, (4) the coding region of the gene of interest (in this case GRG-23(ace3)(R173K).

This *Chlamydomonas* EPSPS CTP/GRG-23(ace3)(R173K) construct was engineered into a vector for use in *Agrobacterium*-mediated transformation of maize embryos, and transgenic events identified.

Figure 2:
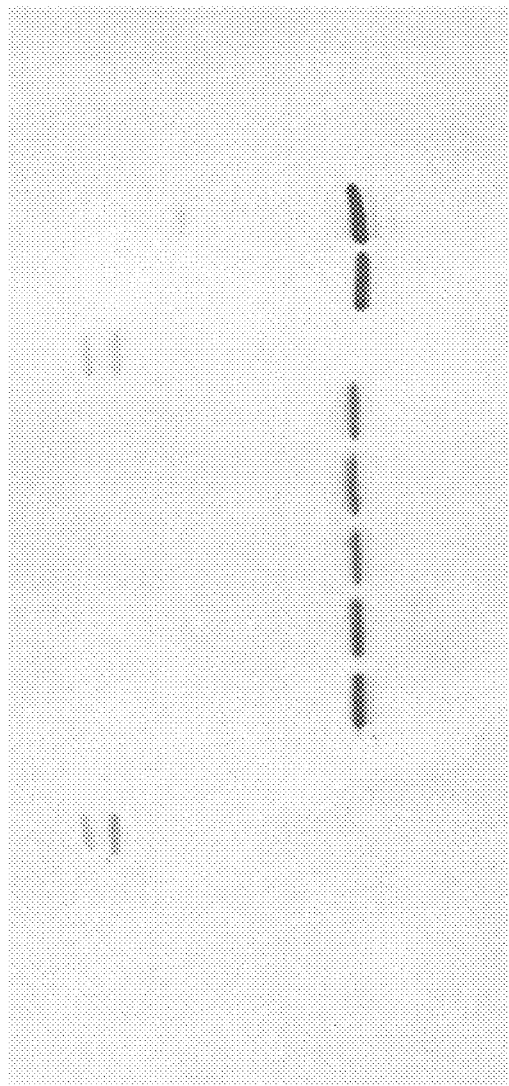
FIG. 2 demonstrates expression and processing of *Chlamydomonas* EPSPS chloroplast transit peptide in maize cells. Lane 1: Non-transgenic maize line Hi-II; Lanes 2-6: Individual T$_o$ events transformed with *Chlamydomonas* EPSPS CTP/GRG23(ace3)(R173K) construct; Lane 7: Protein molecular weight marker; Lane 8: Purified GRG23(ace3) (R173K) protein (4 ng).

$T_0$ transformed plants were analyzed by PCR to confirm presence of the construct in the maize lines, and these $T_0$ plants were then out-crossed to a non-transgenic line to generate hemizygous $T_1$ progeny. The resulting $T_1$ transgenic plants are resistant to spray applications of glyphosate (as compared to non-transgenic controls). Western blots of leaf tissue from transgenic maize plants were found to express the *Chlamydomonas* EPSPS CTP/GRG-23(ace3)(R173K) protein. The protein detected in plant tissues is smaller than the full-length *Chlamydomonas* EPSPS—GRG-23(ace3)(R173K) protein, and is similar in size to the native GRG-23(ace3)(R173K) protein (FIG. 2). The ability of the *Chlamydomonas* EPSPS CTP/GRG-23(ace3)(R173K) protein to confer herbicide resistance and the size of the resulting mature GRG-23(ace3)(R173K) protein in herbicide resistant plants are both consistent with import of the protein into chloroplasts, and processing of the *Chlamydomonas* EPSPS CTP/GRG-23(ace3)(R173K) protein at or near the cleavage site.

Example 10

Figure 3:
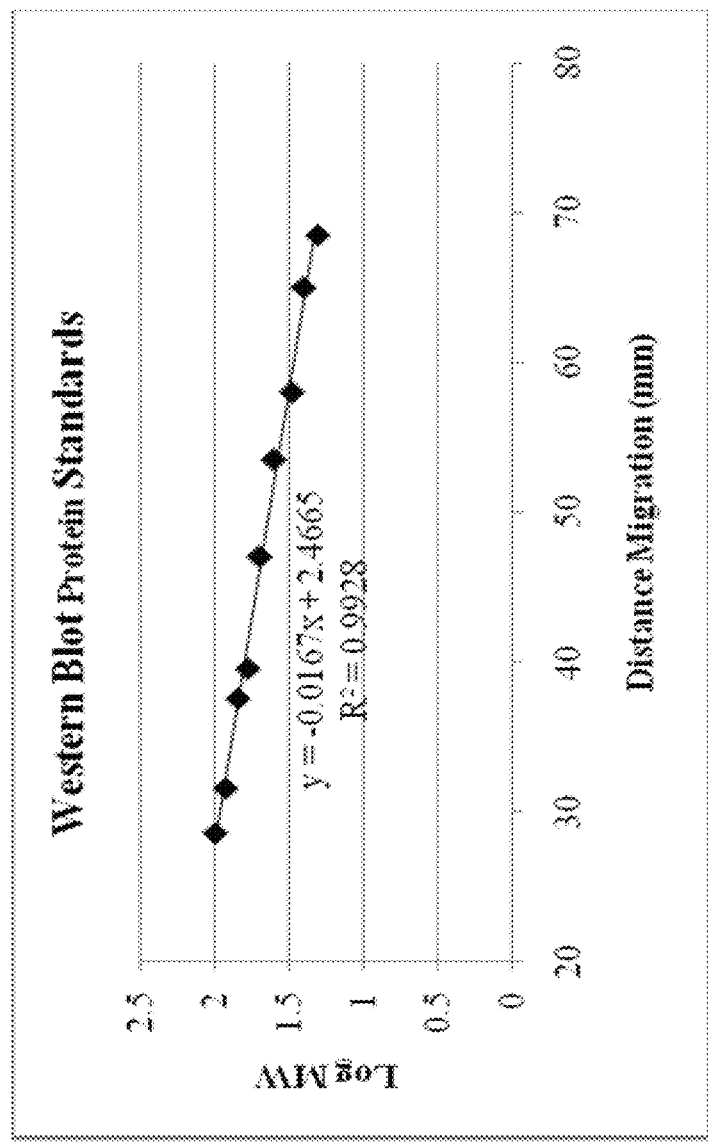
FIG. 3 demonstrates the calculation of the molecular weight of the processed *Chlamydomonas* EPSPS—GRG-23 (ace3)(R173K) protein expressed in maize. A linear regression of the plot of Log Molecular Weight vs. Distance Migration of the protein molecular weight standards from FIG. 2 was used to calculate the apparent molecular weight of the GRG23(ace3)(R173K) protein standard and the processed *Chlamydomonas* EPSPS—GRG-23(ace3)(R173K) detected in plant extract.

Molecular Weight Analysis of *Chlamydomonas* EPSPS—GRG-23(ace3)(R173K) Protein Expressed in Maize From a Western blot of transgenic maize lines expressing *Chlamydomonas* EPSPS—GRG-23(ace3)(R173K) protein, the distance migration of protein molecular weight standards was graphed to generate a linear plot of Log Molecular Weight vs. Distance Migration (FIG. 3). The linear regression equation of this plot was used to calculate the apparent molecular weight of the GRG23(ace3)(R173K) protein standard (FIG. 2, lane 8) and of the processed *Chlamydomonas* EPSPS—GRG-23(ace3)(R173K) protein detected in plant extract. By this method, the apparent molecular weight of the purified GRG23(ace3)(R173K) protein was determined to be 45,347 grams/mole, and the apparent molecular weight of the processed *Chlamydomonas* EPSPS—GRG-23(ace3)(R173K) (lane 6, distance migration=48.5 mm) was determined as 46,227 grams/mole. The estimated molecular weights of the processed proteins are consistent with processing of the *Chlamydomonas* CTP several amino acids upstream of its junction with GRG-23(ace3)(R173K) (the molecular weight of GRG23(ace3)(R173K) is estimated to be 45,570 grams/mole). No protein of a size consistent with unprocessed *Chlamydomonas* EPSPS—GRG-23(ace3) (R173K) protein (MW=52,012 grams/mole) is detected by Western blot. Therefore, the *Chlamydomonas* EPSPS CTP is processed in maize at a discrete recognition site within the *Chlamydomonas* CTP. Purification and N-terminal amino acid analysis of this protein by methods known in the art would allow unambiguous determination of the exact cleavage site within the *Chlamydomonas* CTP.

ever, the *Chlamydomonas* AHAS CTP construct correctly delivered TagGFP into the chloroplast resulting in accumulation of florescence in the chloroplast of these protoplasts (FIG. 1).

Example 12

Evaluation of an Algal CTP Sequence in Soybean Cells

To assess the ability of algal chloroplast CTPs to function in soybean cells, the ChlamyAHAS CTP construct (pAX3517), the ChlamyEPSPS construct (pAX4562), and a control construct (pAX3521) containing the TagGFP gene without a chloroplast transit peptide were used in polyethylene glycol-mediated transformation of soybean protoplasts. Expression and localization of TagGFP protein following transient expression was monitored under an inverted fluorescent microscope.

For the control construct lacking a chloroplast CTP, Tag-GFP fluorescence was observed only in the cytoplasm. Similarly, no expression in the chloroplasts was observed from two independent constructs expressing TagGFP with the ChlamyEPSPS chloroplast CTP. However, TagGFP was detected in the chloroplast of protoplasts that had been transformed with the ChlamyAHAS chloroplast CTP construct. Thus, this CTP functions in soybean and well as tobacco cells.

TABLE 2

Localization of algal chloroplast CTP-linked proteins in dicot cells.

| Construct | CTP | Gene | Localization of TagGFP in Tobacco Protoplasts | Localization of TagGFP in Soybean Protoplasts |
|---|---|---|---|---|
| pAX3517 | ChlamyAHAS | TagGFP | Chloroplast | Chloroplast |
| pAX4562 | ChlamyEPSPS | TagGFP | not tested | Non-Chloroplast |
| pAX3521 | None | TagGFP | Non-Chloroplast | Non-Chloroplast |

Example 11

Evaluation of Algal CTP Sequences in Dicots

To assess the ability of algal chloroplast CTPs to function in dicot cells, the *Chlamydomonas* AHAS Chloroplast CTP (SEQ ID NO:3) was positioned in frame 5' of TagGFP gene (Evrogen, Moscow, Russia). A control vector contained the TagGFP gene without a chloroplast transit peptide. The ChlamyAHAS CTP construct (pAX3517) and control construct (pAX3521) were organized to initiate transcription from the *Arabidopsis* UBQ3 promoter (Norris et. al, 1993, Plant Molecular Biology 21:895-906). Constructs utilized either 35S or PinII transcriptional terminators.

Approximately twelve micrograms of each purified plasmid was used in polyethylene glycol-mediated tobacco protoplast transformation experiments. After transformation, the protoplasts were incubated in a growth chamber at 25° C. for 23 hours. Expression and localization of TagGFP protein following transient expression was monitored under an inverted fluorescent microscope.

The construct expressing the TagGFP without a chloroplast CTP was detected only in the cytoplasm of protoplasts. How-

TABLE 3

Summary of function of *Chlamydomonas* CTPs in Plant Cells

| CTP | Function in Monocot cells | Function in Dicot Cells |
|---|---|---|
| ChlamySSU | ++ | not tested |
| ChlamyEPSPS | +++ | − |
| ChlamyAHAS | +++ | +++ |

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A monocot plant cell having stably incorporated into its genome an expression cassette comprising a nucleotide sequence encoding a chloroplast targeting peptide (CTP), wherein said nucleotide sequence encoding said CTP is operably linked to a nucleotide sequence of interest, and wherein said nucleotide sequence encoding said CTP is selected from the group consisting of:

a) the nucleotide sequence set forth in SEQ ID NO:6;
   b) a nucleotide sequence encoding the amino acid sequence set forth in SEQ ID NO:7; and,
   c) a nucleotide sequence encoding an amino acid sequence having at least 90% sequence identity to SEQ ID NO:7, wherein said amino acid sequence is a chloroplast transit peptide.

2. A plant comprising the plant cell of claim 1.

3. A seed derived from the plant of claim 2, wherein said seed comprises the nucleotide sequence encoding said chloroplast transit peptide.

4. The plant cell of claim 1, wherein the nucleotide sequence of interest encodes a gene product that confers herbicide, pathogen, or insect resistance.

* * * * *